(12) United States Patent
El Menyawi

(10) Patent No.: US 11,312,746 B2
(45) Date of Patent: Apr. 26, 2022

(54) METHOD AND SYSTEM OF PROTEIN EXTRACTION

(71) Applicant: CSL BEHRING AG, Bern (CH)

(72) Inventor: Ibrahim El Menyawi, Bern (CH)

(73) Assignee: CSL BEHRING AG, Bern (CH)

( * ) Notice: Subject to any disclaimer, the term of this patent is extended or adjusted under 35 U.S.C. 154(b) by 0 days.

(21) Appl. No.: 17/054,018

(22) PCT Filed: May 17, 2019

(86) PCT No.: PCT/EP2019/062757
§ 371 (c)(1),
(2) Date: Nov. 9, 2020

(87) PCT Pub. No.: WO2019/219890
PCT Pub. Date: Nov. 21, 2019

(65) Prior Publication Data
US 2021/0246162 A1    Aug. 12, 2021

(30) Foreign Application Priority Data
May 17, 2018  (EP) ........................................ 8172904

(51) Int. Cl.
| C07K 1/36 | (2006.01) |
| C07K 1/16 | (2006.01) |
| C07K 1/30 | (2006.01) |
| C07K 1/34 | (2006.01) |
| C07K 16/00 | (2006.01) |

(52) U.S. Cl.
CPC .................. C07K 1/36 (2013.01); C07K 1/16 (2013.01); C07K 1/30 (2013.01); C07K 1/34 (2013.01); C07K 16/00 (2013.01)

(58) Field of Classification Search
CPC ... C07K 1/36; C07K 1/30; C07K 1/34; C07K 16/00
See application file for complete search history.

(56) References Cited

U.S. PATENT DOCUMENTS

| 6,106,713 A | * | 8/2000 | Miller .................. | B01D 29/055 210/321.63 |
| 2004/0167320 A1 | | 8/2004 | Couto et al. | |
| 2011/0130545 A1 | | 6/2011 | Hensgens et al. | |

FOREIGN PATENT DOCUMENTS

| EP | 1247818 A2 * | 10/2002 | ........... C07K 16/065 |
| EP | 2583744 A1 * | 4/2013 | ............. B01D 61/20 |
| WO | WO-2005/007269 A1 | 1/2005 | |

OTHER PUBLICATIONS

Castilho et al., "An Integrated Process for Mammalian Cell Perfusion Cultivation and Product Purification Using a Dynamic Filter," Biotechnol. Prog., vol. 18, No. 4, pp. 776-781 (Jul. 2002).

\* cited by examiner

*Primary Examiner* — Daniel E Kolker
*Assistant Examiner* — James L Rogers
(74) *Attorney, Agent, or Firm* — Foley & Lardner LLP

(57) ABSTRACT

The present invention relates to a method and a system of extracting a protein with high yield from a protein-comprising precipitate, in particular immunoglobulin, from human or non-human origins, such as blood plasma.

29 Claims, 2 Drawing Sheets

METHOD AND SYSTEM OF PROTEIN EXTRACTION

CROSS-REFERENCE TO RELATED APPLICATIONS

The present application is the U.S. National Stage of International Application No. PCT/EP2019/062757, filed May 17, 2019, and claims priority to European Patent Application No. 18172904.7 filed May 17, 2018.

TECHNICAL FIELD

The present invention relates to a method and system for extracting proteins from precipitates, particularly recombinant and/or plasma derived proteins including immunoglobulins (Ig) such as immunoglobulin G (IgG).

BACKGROUND OF THE INVENTION

The demand for purified proteins such as specific antibodies has increased considerably. Such purified proteins can be used for therapeutic and/or diagnostic purposes.

Human blood plasma has been industrially utilized for decades for the production of widely established and accepted plasma-protein products such as e.g. human albumin (HSA), immunoglobulin (IgG), clotting factor concentrates (clotting Factor VIII, clotting Factor IX, prothrombin complex etc.) and inhibitors (antithrombin, C1-inhibitor etc.). In the course of the development of such plasma-derived drugs, plasma fractionation methods have been established, leading to intermediate products enriched in certain protein fractions, which then serve as the starting composition for plasma-protein product/s. Typical processes are reviewed in e.g. Molecular Biology of Human Proteins (Schultze H. E., Heremans J. F.; Volume I: Nature and Metabolism of Extracellular Proteins 1966, Elsevier Publishing Company; p. 236-317) and simplified schematics of such processes are given. These kinds of separation technologies allow for the production of several therapeutic plasma-protein products from the same plasma donor pool. This is economically advantageous over producing only one plasma-protein product from one donor pool, and have therefore been adopted as the industrial standard in blood plasma fractionation.

In particular the cold ethanol fractionation of plasma was pioneered by E. J Cohn and his team during World War II, primarily for the purification of albumin (Cohn E J, et al. 1946, J. Am. Chem. Soc. 62: 459-475). The Cohn fractionation process involves increasing the ethanol concentration in stages, from 0% to 40%, while lowering the pH from neutral (pH 7) to about 4.8, resulting in the precipitation of albumin. Whilst Cohn fractionation has evolved over the past 70 years or so, most commercial plasma fractionation processes are based on the original process or a variation thereof (e.g. Kistler/Nitschmann), exploiting differences in pH, ionic strength, solvent polarity and alcohol concentration to separate plasma into a series of major precipitated protein fractions (such as Fractions I to V in Cohn).

Variations to the Cohn Fractionation have been developed with the aim of improving polyvalent IgG recoveries. For example Oncley and co-workers used Cohn Fractions II+III as a starting material with different combinations of cold ethanol, pH, temperature and protein concentration to those described by Cohn, to produce an active immune globulin serum fraction (Oncley et al., (1949) J. Am. Chem. Soc. 71, 541-550). Today, the Oncley method is the classic method used for production of polyvalent IgG. Nevertheless, it is known that approximately 5% of gamma-globulins (antibody-rich portion) is co-precipitated with Fraction I and about 15% of the total gamma-globulin present in plasma is lost by the Fraction II+III step (See Table III, Cohn E J, et al. 1946, J. Am. Chem. Soc. 62: 459-475). The Kistler/Nitschmann method aimed to improve IgG recovery by reducing the ethanol content of some of the precipitation steps (Precipitation B vs Fraction III). The increased yield, however, is at the expense of the purity (Kistler & Nitschmann, (1962) Vox Sang. 7, 414-424).

Initially, immunoglobulin G (IgG) preparations derived from these fractionation processes were successfully used for the prophylaxis and treatment of various infectious diseases. However as ethanol fractionation is a relatively crude process the IgG products contained impurities and aggregates to an extent that they could only be administered intramuscularly. Since that time additional improvements in the purification processes have led to IgG preparations suitable for intravenous (called IVIg) and subcutaneous (called SCIg) administration.

It has been estimated that approximately 30 million liters of plasma were processed worldwide in 2010, providing a range of therapeutic products including about 500 tonnes of albumin and 100 tonnes of IVIG. The IVIG market accounts for about 40-50% of the entire plasma fractionation market (P. Robert, Worldwide supply and demand of plasma and plasma derived medicines (2011) J. Blood and Cancer, 3, 111-120). Thus, with demands for IVIG remaining strong (along with increasing demands for SCIG) there remains a need to improve immunoglobulin recoveries from plasma and related fractions. Preferably, this must be achieved in a way that ensures the recovery of other plasma derived therapeutic proteins are not adversely affected.

From a commercial perspective, the initial fractionation processes are critical to the overall production time and costs associated with the production of a therapeutic protein, particularly plasma derived proteins, since the subsequent purification steps will depend on the yield and purity of the protein(s) of interest within these initial fractions. Whilst several variations of cold ethanol fractionation process have been developed for plasma derived protein in order to improve protein yield at lower operating costs, higher protein yields are typically associated with lower purity. The present invention provides a method of fractionating protein-containing precipitates, particularly immunoglobulin G that achieve a greater yield. In particular embodiments the improved recovery in the protein of interest is achieved, whilst minimizing the level of impurities and/or losses in other therapeutic proteins.

One of the separation techniques widely used in the plasma fractionation/biotechnology field is membrane filtration, wherein membrane filtration is a pressure driven separation process to separate components based on their size and/or their charge. There are two main membrane filtration methods, namely i) single pass or direct flow filtration; and ii) crossflow or tangential flow filtration.

Conventional tangential flow systems are designed to control the fluid flow pattern of a feedstream so as to enhance transport of the retained solute away from the fixed membrane surface and back to the bulk of the feed. In this way the feedstream can be re-circulated at high velocities at a vector tangential to the plane of the membrane to increase the mass-transfer coefficient to allow for back-diffusion and to clean the membrane surface to prevent clogging. In such filtration processes a pressure differential is applied along the length of the membrane to cause the fluid and filterable solutes to flow through the filter. The solution may be passed repeatedly over the membrane while said fluid which passes through the filter is continually drawn off into a separate unit. However, limitations exist on the degree of achievable protein purification mainly due to phenomena of concentration polarization, fouling and the relatively wide distribution in the pore size of most membranes. Hence, it is known that the effective use of the macromolecular fractionation capabilities of ultrafiltration membranes for the large-scale resolution of macromolecular mixtures such as blood plasma proteins is generally not practical.

US 2004/0167320 discloses a process and an apparatus for separating molecules, including immunoglobulins, from complex mixtures such as milk (which typically contains 87% water and 13% solids) using methods of conventional tangential flow filtration and microfiltration. The process comprises a clarification, a concentration/filtration and an aseptic filtration step employing three filtration unit operations. The clarification step removes larger particulate from the product and the concentration/filtration step removes most small molecules to increase the purity and reduce the volume of the resulting product composition. The clarifying and the concentration/filtration steps are performed by pumping the feed in a loop to concentrate either the retentate or the permeate. The first and the second step are sized and timed to be processed together wherein the permeate from the second step is returned to the first step and is mixed with the retentate of the first step. Once 95% of the product is accumulated in the retentate of the ultrafiltration, the clarification is stopped and a concentration/diafiltration of the ultrafiltration material is begun, wherein the product is concentrated and buffer is added to the ultrafiltration feed tank to wash away the majority of the small molecular weight proteins.

US 2011/0130545 A1 discloses a process for producing secretory immunoglobulin A (S-IgA) compositions from S-IgA-containing milk which uses one or more microporous membrane filtration steps. The process comprises steps of de-fatting, microfiltration and ultrafiltration through a number of diafiltration cycles, wherein the microfiltrated retentate is combined with a diafiltration liquid. The combination of microfiltrated retentate and diafiltration liquid is then subjected to subsequent microfiltration and concentration steps. The process used is a continuous diafiltration. The disclosed process is based on the membrane filtration technique, wherein the essential feature is that particles suspended in a liquid feedstream are separated on the basis of their size.

EP1262225 discloses a continuous system for the production of an emulsion using one or more membranes through which one liquid is dispersed continuously into another liquid to achieve a continuous phase.

There is a need for an improved method and system for the industrial scale production of proteins such as immunoglobulins from immunoglobulin-comprising precipitate material, for example derived from plasma or serum, which have to meet stringent safety standards. The currently used downstream technologies are relatively expensive and their yield is not optimal. In addition conventional filtration systems with fixed membranes have a tendency to foul rapidly in the presence of solutions containing resuspended protein precipitates; these are some of the problems which have to be overcome. Therefore, there is a crucial need to develop more efficient, economic and faster methods for the extraction and purification of proteins such as immunoglobulins from protein containing suspensions.

SUMMARY OF THE INVENTION

The inventor of the present invention has found an effective solution for the above-discussed problems by introducing a new method and a new system, in particular the first process unit, as presently claimed. The method according to the invention provides a cost-effective, high efficiency and a reliable solution to the existing problems.

According to a first aspect of the invention, there is provided a method for extracting a protein of interest from a precipitate, comprising:
  a. mixing the precipitate with a liquid in a first tank to form a suspension having a first dilution factor;
  b. feeding the suspension into a first filtration unit comprising a dynamic filter element adapted to produce a first retentate and a first permeate enriched with the protein of interest;
  c. diluting the suspension in the first tank by adding liquid to a second dilution factor, optionally by streaming the first retentate into the first tank; and
  d. recovering the first permeate enriched with the protein of interest in a second tank.

Protein precipitation is widely used in downstream processing of biological products in order to concentrate proteins and purify them from various contaminants. The underlying mechanism of precipitation is to alter the solvation potential of the solvent, more specifically, by lowering the solubility of the solute (i.e. the protein) by addition of a reagent and/or modulating the conditions (e.g. like pH or conductivity). The ensuing precipitate is an insoluble solid that comprises the protein of interest. Often it is in the form of a pellet or a paste. Sometimes the precipitate can emerge as a suspension. The solid portion may then be collected by for example filtration and/or centrifugation. Alternatively such a suspension may be added directly to the first tank to form the first dilution factor. Another option is to add the suspension to the first tank and then add liquid to the first tank to form the first dilution factor. Thus in a particular embodiment the precipitate comprising the protein of interest is in the form of a suspension when added to the first tank.

This method is especially suitable for industrial scale to yield the protein of interest. According to one embodiment of the first aspect of the present invention the method to extract protein is an industrial scale process.

In a further embodiment, the precipitate comprising the protein of interest is an intermediate product of an alcohol fractionation process, preferably of blood plasma, more preferably of human blood plasma. In preferred embodiments the precipitate is obtained from a human plasma starting material. Even more preferably the precipitate is obtained from 2500 L to 6000 L of a human plasma starting material.

According to another embodiment of the first aspect of the present invention the precipitate is a plasma fraction (intermediate). In particular embodiments the fraction is a Cohn Fraction. In a preferred embodiment the plasma fraction is selected from the group consisting of Cohn Fraction I (Fr I), Cohn Fraction II+III (Fr II+III), Cohn Fraction I+II+III (Fr I+II+III), Cohn Fraction II (Fr II), Cohn Fraction III (Fr III), Cohn Fraction IV (Fr IV), Cohn Fraction V (Fr V), Kistler/Nitschmann Precipitate A (KN A), Kistler/Nitschmann Precipitate B (KN B), Kistler/Nitschmann Precipitate C (KN C). In a particularly preferred embodiment the plasma fraction is selected from the group consisting of Cohn Fraction I (Fr I), Cohn Fraction II+III (Fr II+III), Cohn Fraction I+II+III (Fr I+II+III), or Kistler/Nitschmann Precipitate A (KN A). The plasma fraction may be a combination of different fractions. For example, the plasma fraction may be a combination of KN A and one or more of Fr I, Fr II+III and Fr I+II+III. In another embodiment the precipitate is an octanoic acid precipitate.

In another embodiment, the protein-comprising precipitate is obtained from a culture supernatant or a fermentation starting material. In some embodiments the starting material is milk comprising the protein of interest. In other embodiments the starting material is not milk.

According to a further embodiment, the protein of interest is an immunoglobulin, preferably human immunoglobulin G (IgG) such as immunoglobulin G from human plasma or a recombinantly produced immunoglobulin G.

According to another embodiment of the present invention, the suspension is produced by mixing the protein-comprising precipitate with a liquid such as a buffer or water, thereby providing the starting composition with the first dilution factor. When the protein-comprising precipitate is almost solid (e.g. very thick paste, pellet or etc), addition of a liquid to the protein-comprising precipitate allows a suspension to be formed as the starting composition.

The suspension having a first dilution factor of step a) is a mixture in which solute-like particles, sometimes herein referred to as solids, are present in the solution. The size of the particles can vary and includes larger particles that will eventually settle if the solution is not mixed or smaller sized particles that do not settle (i.e. in the form of a colloid).

The first dilution factor can sometimes be referred to as percent solids by weight (% w/v). This is defined as the weight of dry solids in a given volume of the suspension, divided by the total weight of that volume of the suspension, multiplied by 100. In particular embodiments the percent solids per weight of the suspension of step a) is at least 5% (i.e. a first dilution factor of about 1:20), or at least 7.5% or at least 10%, or at least 12.5%, or at least 15%, or at least 17.5%, or at least 20% or at least 22.5% or at least 25% or at least 27.5%, or at least 30%, or at least 35%, or at least 40%, or at least 50%. In some embodiments the percent solids per weight of the suspension of step a) is from 10% to 30%. In some embodiments the percent solids per weight of the suspension of step a) is from 15% to 25%. In preferred embodiments the percent solids per weight of the suspension of step a) is from 17.5% to 22.5%. In a particular embodiment the percent solids per weight of the suspension of step a) is 20%.

According to another embodiment of the present invention, the first dilution factor is at least 3 (1:3; parts precipitate:total), preferably between 1 to 10, preferably between 3 to 9, preferably between 3 to 5, preferably about 3, 5, 6, 7, 9 or 10. For example, when the protein-comprising precipitate is a pellet or a paste, and in particular a very thick paste (with very high viscosity), a liquid is required to suspend the paste or the pellet.

For example, when the first dilution factor is 3 (1:3; 1 part of the protein-comprising precipitate:total), this equates to a dilution ratio of 1:2 (1 unit volume of solute (the material to be diluted) with 2 unit volumes of the diluent to give 3 total units of total volume).

In another embodiment, the first dilution factor (protein-comprising precipitate:total) in the first tank is at least 40, or at least 30, or at least 20, or at least 17.5, or at least 15, or at least 12.5, or at least 10, or at least 9, or at least 8, or at least 7, or at least 6, or at least 5.5, or at least 5, or at least 4.5, or at least 4, or at least 3.5, or at least 3, or at least 2.5, or at least 2, or at least 1.5, or at least 1.25. Preferably the first dilution factor (protein-comprising precipitate:total) in the first tank is at least 4.

In some embodiments the first dilution factor (protein-comprising precipitate:total) in the first tank is between 1:1 to 1:20, or is between 1:2 to 1:20, or is between 1:3 to 1:20, or is between 1:4 to 1:20, or is between 1:5 to 1:20, or is between 1:6 to 1:20, or is between 1:7 to 1:20, or is between 1:8 to 1:20, or is between 1:10 to 1:20, or is between 1:1 to 1:15, or is between 1:2 to 1:15, or is between 1:3 to 1:15, or is between 1:4 to 1:15, or is between 1:5 to 1:15, or is between 1:6 to 1:15, or is between 1:7 to 1:15, or is between 1:8 to 1:15, or is between 1:10 to 1:15, or is between 1:1 to 1:10, or is between 1:2 to 1:10, or is between 1:3 to 1:10, or is between 1:4 to 1:10, or is between 1:5 to 1:10, or is between 1:6 to 1:10, or is between 1:7 to 1:10, or is between 1:8 to 1:10, or is between 1:9 to 1:10, or is between 1:3 to 1:7, or is between 1:3 to 1:8, or is between 1:3 to 1:9, or is between 1:4 to 1:7, or is between 1:4 to 1:8, or is between 1:4 to 1:9, or is between 1:5 to 1:7, or between 1:5 to 1:8, or between 1:5 to 1:9, or is between 1:3.5 to 1:5, or is between 1:4 to 1:5, or is between 1:1 to 1:3, preferably 1:9, 1:7, 1:5 or more preferably 1:3 or 1:1.

Suitably, the protein in a protein comprising precipitate after resuspension is at a concentration of about 5-100 g/L, preferably 10-50 g/L or more preferably 25-45 g/L. This includes 5, 10, 15, 20, 25, 30, 35, 40, 45, 50, 55, 60, 65, 70, 75, 80, 85, 90, 95 and 100 g/L and any ranges between these amounts. In other embodiments, the protein may be at a concentration of from about 5-20 g/L, e.g. about 8-12 g/L.

According to a preferred embodiment, the suspension in the first tank has a pH of between about 3.0 and 9.0, preferably between about 4.0 and 7.0, between about 4.0 to 6.0, between about 4.0 to 5.0, between about 4.3 to 4.9, between about 4.4 to 4.8, more preferably about 5.0. In general, the pH is measured either in the solution before adding the protein precipitate to the solution; or directly after mixing the protein precipitate with the solution. Typically, the pH of the solution is measured right after mixing the precursor components. Alternatively, the pH can also be determined by calculation based on the projected amounts and concentrations of the components in the mixture.

According to an embodiment of the first aspect of the present invention the suspension is continuously fed into the first filtration unit. In a preferred embodiment the suspension is continuously fed into the first filtration unit until the suspension has been diluted to at least the second dilution factor. In another embodiment of the present invention, the continuous separation process is a continuous filtration process where one or more filtration membranes or different types of filtration membranes can be used. The continuous filtration process such as a dynamic cross-flow filtration can minimize the risk of the filtration members being blocked.

As the method of the first aspect of the invention involves adding additional liquid to the suspension in the first tank the second dilution factor is greater than the first dilution factor.

According to an embodiment of the first aspect of the present invention the second dilution factor (volume of protein-comprising precipitate to volume of total recirculated liquid) is between 6 and 70, between 10 and 70, about 10, about 20, about 30, about 40, preferably about 20 to 50. In other embodiments the second dilution factor is about 60, or about 70 (1:70; parts protein-comprising precipitate:total). In particular embodiments the second dilution factor is at least 20, or at least 30, or at least 40, or at least 50, or at least 60, or at least 70. The inventor of the present invention found that such high dilution factors could enhance extraction efficiency, thus giving an improved yield.

In yet another embodiment, the predetermined value of protein concentration in the suspension is less than 0.1 g/L, preferably between about 0.001 to 0.1 g/L; typically between about 0.05 to 0.1 g/L. Such value is provided such that the separation process can be terminated immediately once such threshold is reached in order to avoid inefficient extraction and filtration processes. For instance, when the total protein concentration in the suspension or the solution is less than 0.1 g/L, the total amount of IgG is estimated to be less than about 40-50 mg/L, which makes it less economical to continue the continuous extraction and filtration of the product of interest.

According to an embodiment of the first aspect of the present invention the dynamic filter element in the first filtration unit is a dynamic cross flow filter element. In a preferred embodiment the dynamic cross flow filter element is a rotational cross flow filter element. More preferably the rotational cross flow filter element comprises a filter disc. The filter discs are usually mounted on a shaft member. In an embodiment the rotational cross flow filter element comprises at least one filter disc and at least one shaft member.

According to a preferred embodiment of the first aspect of the present invention the filter disc membrane is a ceramic membrane. More preferably the ceramic membrane has a pore size in the range of greater than or equal to 50 nm to less than or equal to 100 nm. Such filter discs are supplied by Kerafol and Flowserve.

The first filtration unit in preferred embodiments comprises a pressure vessel. The suspension from the first tank can be continuously fed into the pressure vessel via an inlet port. An even distribution of the suspension in the vessel can be achieved using a distribution manifold. Hence in particular embodiments the pressure vessel comprises a distribution manifold. In some embodiments the first filtration unit comprises a rotational cross flow filter element. Preferably the filter element contains more than one filter disc evenly spaced along at least one hollow central collection shaft. The filter discs can be arranged either horizontally or vertically. When in the horizontal orientation they are spaced along a vertically orientated hollow collection shaft. The collection shaft and discs are rotatable. The suspension in the pressure vessel can then penetrate the outer membrane of the rotating filter discs so as to pass through into a hollow central portion of the disc which is in turn channeled into the central collection shaft. Typically the filtrate (i.e. the first permeate enriched in the protein of interest) can then be removed from the shaft portion of the first filtration unit via a flanged port. Whilst the retentate remaining in the pressure housing can be fed out of the vessel via an outlet port. Generally the retentate is recirculated to the first tank to dilute the suspension. In this way the retentate from the first filtration unit can be utilised to dilute the suspension in the first tank to a second dilution factor.

Dynamic cross flow filtration such as rotational filtration provides maximum filter efficiency. The cross flow effect (tangential flow cleaning of the filter surface) is generated by rotating the filter discs and not by pumping large volumes across a fixed membrane as used in conventional (static) cross flow filtration systems. The extreme cross flow velocities generated at the surfaces of the rotating filter discs ensure a highly efficient cleaning of the filter surface, whilst consuming very low amounts of energy compared to conventional cross flow techniques.

The temperature has an effect on the viscosity of a protein solution and also has an effect on the flux upon filtration with a membrane. The starting suspension to be used in the method of the invention should have a temperature within the range from 0° C. up to the temperature at which the protein concerned is denatured. The temperature suitably is within the range of from about 10° C. up to about 50° C. In particular embodiments the temperature is within the range of from about 18° C. up to about 35° C. According to one preferred embodiment, the temperature in the first process unit is controlled, preferably between 2 and 25° C., more preferably at about 2 to 10° C. Such temperature ensures an optimum extraction process and separation process while maintaining the bio-reactivity of the protein of interest throughout the processes.

Filtration is performed with a transmembrane filtration pressure that is the same as or below the level at which the membrane can withstand, depending on the material of the membrane to be used herein, for example with pressures of about 0.2 to about 3 bar. The transmembrane pressure is typically from 0.1 to 2.5 bar, preferably from 0.2 to 2.4 bar, more preferably from 0.4 to 2.0 bar, from 0.5 to 1.8 bar, from 0.6 to 1.6 bar, from 0.6 to 1.5 bar, from 0.7 to 1.5 bar, most preferably from 0.8 to 1.5 bar. According to another embodiment, a pressure of up to 2 bar, preferably between 0.1 to 2.0 bar, or about 1.5 bar, 1.0 bar or 0.5 bar is provided to the first process unit.

According to another embodiment, the continuous extraction process is further assisted by regulating the flow rate and/or the residence time of the suspension or the solution into the first process unit and/or the flow rate of the first retentate/raffinate and/or the flow rate of the first permeate/extract. For instance, in one embodiment, the linear velocity of the suspension or the solution into the pressure vessel (first process unit) can be about 0.27 to 1.66 m/s. In another example, the linear velocity of the first retentate can be 0.25 to 1.33 m/s. In another example, the linear velocity of the first permeate/extract can be 0.03 to 0.33 m/s. Linear velocity multiplied by the cross-sectional area gives the volumetric flow rate. In addition, a turbulence can be created in the first process unit as a result of the speed of the rotating filter discs, wherein the speed (sometimes referred to as tangential speed) can be between about 1 to 7 m/s. According to an embodiment of the present invention, the speed of the rotating disc filters is between 1 to 10 m/s. In a preferred embodiment of the present invention, the speed of the rotating disc filters is between 5 to 7 m/s. More preferably the speed of the rotating disc filters is 7 m/s at 60 Hertz (800 rpm). The rotating speed of the rotational cross-filter element is between about 600 rpm (50 Hz) and about 1600 rpm (100 Hz), preferably between about 800 rpm (60 Hz) and about 1200 rpm (80 Hz), preferably about 800 rpm (60 Hz), about 1000 rpm (70 Hz) or about 1200 rpm (80 Hz). As used herein, the rotating speed in Hz is intended to refer to the speed of the motor. This can be correlated with the speed in rpm using an appropriate calibration curve.

This method allows a continuous extraction and a separation process to be realised for maximising the recovery of the protein of interest from the starting precipitate/material. Thanks to the extraction process, almost all the protein of interest is extracted from the protein-comprising precipitate and is recovered in subsequent stages. This method also allows the liquid or diluent e.g. buffer or water to be re-circulated in a closed system and hence the quantity of the liquid is maintained throughout the process while footprints (i.e. large tank volume) can be reduced. It is estimated that the method and the system disclosed herein recovers at least 95%, or typically at least 98% of the protein of interest of the originally present protein of interest in the protein-comprising precipitate. Hence in particular embodiments of the first aspect of the present invention the method provides a recovery of at least 95%, or at least 96%, or at least 97%, or at least 98% or at least 99% of the protein of interest from the precipitate. In a preferred embodiment the recovery is at least 97% of the protein of interest from the precipitate.

The first permeate in the second tank can be subjected to an concentration step. According to a preferred embodiment of the first aspect of the present invention, the concentration process is an ultrafiltration performed in a second process unit.

According to a preferred embodiment of the first aspect of the present invention the method additionally comprises subjecting the first permeate in the second tank to a continuous concentration process in a second filtration unit, thereby producing a second retentate enriched with the protein of interest and a second permeate depleted of the protein of interest.

According to an embodiment of the first aspect of the present invention the second filtration unit comprises a dynamic cross flow filter element.

In preferred embodiments of the invention the dynamic cross flow filter element or the ultrafiltration filter device comprises a membrane with a molecular weight cutoff less than the molecular weight of the protein of interest. In these embodiments the membrane cutoff is selected to retain the protein of interest in the second retentate. As a general guide a nominal membrane cutoff at least 3 fold lower than the molecular weight of the protein of interest can be selected to ensure the protein is retained in the retentate. In an embodiment the dynamic cross flow filter element or the static ultrafiltration filter element comprises a membrane with a molecular weight cutoff greater than the molecular weight of the protein of interest. In such embodiments the nominal membrane cutoff is selected to ensure the protein of interest passes across the membrane and is collected in the second permeate.

According to an embodiment of the first aspect of the present invention the method further comprises diluting the suspension in the first tank by continuously streaming the second permeate or second retentate depleted in the protein of interest to the first tank, thereby contributing to the suspension being diluted to the second dilution factor.

According to an embodiment of the first aspect of the present invention the method further comprises diluting the suspension in the first tank by continuously streaming the retentate from the first filtration unit and the second permeate from the second filtration unit into the first tank, thereby diluting the suspension to the second dilution factor.

According to yet a further preferred embodiment, a second tank is provided to receive the first permeate and/or the second retentate, wherein the flow velocity of the first permeate and the second permeate are controlled such that a substantially constant product volume is maintained in the second tank. In particular embodiments fresh buffer is added to the first tank in addition to the the first permeate and/or the second retentate.

According to an embodiment of the first aspect of the present invention, the first permeate/extract is collected in a holding tank (second tank), and once the suspension of the first tank is completely filtrated/extracted, the first permeate/extract from the holding tank is subjected to the continuous concentration process. Such a method step is especially suitable for a smaller industrial scaled process where dead volumes in the production equipment and tubing can significantly impact the yield of the protein of interest. An example is hyperimmune immunoglobulin products.

According to a preferred embodiment of the first aspect of the invention, there is provided an industrial scaled method for extracting a protein of interest in high yield from a precipitate, comprising:
  a. mixing the precipitate with a liquid in a first tank to form a suspension having a first dilution factor;
  b. feeding the suspension into a first filtration unit comprising a rotational cross flow filter element comprising a filter disc having a ceramic membrane with an average pore size between 5 nm and 5000 nm, the filter element adapted to produce a first retentate, and a first permeate enriched with the protein of interest;
  c. diluting the suspension in the first tank by adding liquid to a second dilution factor in part by streaming the first retentate into the first tank;
  d. recovering the first permeate enriched with the protein of interest in a second tank; and
  e. subjecting the first permeate in the second tank to a continuous concentration process in a second filtration unit comprising a cross flow filter element, thereby producing a second retentate enriched with the protein of interest and a second permeate depleted of the protein of interest;
  f. optionally diluting the suspension in the first tank by continuously streaming the second permeate to the first tank, thereby diluting the suspension to the second dilution factor; and
  g. either returning the second retentate enriched with the protein of interest to the second tank and/or collecting the second retentate enriched with the protein of interest.

According to a preferred embodiment of the invention the first retentate and the second permeate are continuously streamed into the first tank to dilute the suspension to the second dilution factor.

According to an embodiment of the invention the first filtration unit further comprises an adjustable scraping device adapted to control the bed height of filter aid and/or precipitate material on an external surface of the ceramic filter disc membrane.

According to an embodiment of the invention the first filtration unit comprises more than one hollow shaft adapted to collect the first permeate, each shaft connected to at least one filter disc comprising a ceramic membrane.

According to an embodiment of the invention the second filtration unit comprises a dynamic cross flow filter element. In other embodiments the second filtration unit comprises a static cross flow filter element. In a preferred embodiment the static cross flow filter element is a ultrafiltration device comprising a membrane that retains the protein of interest in the second retentate.

According to an embodiment of the present invention, either the steps b) to c) or the steps b) to f) are repeated until either a second dilution factor or a predetermined value of protein concentration of the suspension or the solution in the first tank has been achieved. Such predetermined second dilution factor (sometimes referred to as a final dilution factor), which can also be determined using a predetermined value of protein concentration in Tank 1, ensures that an optimal yield can be harvested before it becomes too uneconomical to continue the extraction process. Protein concentration can be monitored in Tank 1 by various methods known in the art including UV absorbance, such as at 280 nm.

Optionally a filter aid may be employed at appropriate stages of the process. A filter aid may be used, for example, in one or more steps involved in preparation of the precipitate. Accordingly, in one embodiment, the precipitate comprises a filter aid. In one embodiment, the precipitate does not comprise filter aid. In this embodiment, a filter aid may not have been used in the process at all (including in any preceding steps), or, if present, is removed prior to feeding the suspension comprising the precipitate into the first filtration unit i.e. before step b). Preferably, the filter aid is removed prior to step b).

The methods according to the first aspect of the invention are suitable for extracting a protein of interest from other protein containing solids. Examples include lyophilisates and crystalized solid forms comprising the protein of interest.

The product of the methods described above may then be subjected to further processing including one or more of chromatography steps, virus inactivation steps, concentration and formulation such that the end product is suitable for administration to a subject, preferably a human subject.

According to a second aspect of the invention, there is provided a closed system for extracting a protein of interest from a precipitate, comprising
  a. a first tank adapted to contain the precipitate in the form of a suspension having a first dilution factor;
  b. a first filtration unit comprising a dynamic filter element, in connection with the first tank for receiving the suspension and the filter element adapted to produce a first permeate enriched with the protein of interest and a first retentate depleted of the protein of interest, wherein the first filtration unit is adapted to return the first retentate to the first tank;
  c. a second tank in connection with the first filtration unit for recovering the first permeate enriched with the protein of interest;
  d. a second filtration unit for concentrating the first permeate in the second tank, adapted to produce a second retentate enriched with the protein of interest and a second permeate depleted in the protein of interest, wherein the second unit is optionally adapted to return the second retentate to the second tank and/or the second permeate to the first tank.

The closed system of the present invention reduces cost of goods such as water, buffers and chemicals needed for the separation of the protein of interest, and also reduces space or footprints of the entire system compared to other commonly used systems while allowing high yield recovery to be achieved.

According to an embodiment of the second aspect of the invention the first filtration unit further comprises a scraper device adapted to control the bed height of filter aid and/or precipitate material on an outer surface of a filter disc membrane. This device can also assist in controlling filtration flux rates and/or prevent filter blockage. In some embodiments the scraping device is height adjustable with respect to the distance to the surface of the filter disc membrane. In particular embodiments the scraping device is positioned at least 20 cm, or at least 15 cm, or at least 10 cm, or at least 9 cm, or at least 8 cm, or at least 7 cm, or at least 6 cm, or at least 5 cm, or at least 4 cm, or at least 3 cm, or at least 2.5 cm, or at least 2 cm, or at least 1.5 cm, or at least 1 cm, or at least 0.5 cm, or at least 0.25 cm from a filter disc membrane.

According to another embodiment of the second aspect of the present invention, the second process unit comprises an ultrafiltration device.

According to a further embodiment, the first filtration process unit is equipped with rotating filter discs (dynamic filter element) and optionally baffles for turbulence mixing of the content of the first process unit, preferably the tangential speed of the disks is between about 1 to 7 m/sec. Turbulences can be produced by the baffles such that extraction of the protein of interest can be increased, thereby high protein recovery yield is achieved.

According to a further preferred embodiment, the first filtration element comprises a filtration membrane having an average pore size of between 5 nm to 5000 nm, preferably between 5 nm to 2000 nm, between 5 nm to 1000 nm, between 5 nm to 500 nm, between 5 nm to 200 nm, between 7 nm to 1000 nm, more preferably between 7 nm to 500 nm, even more preferably between 7 nm to 100 nm, most preferably between 7 nm to 80 nm. Of course, the average pore size can be in other combinations of the range given above. Filter manufacturers often assign terms like nominal or mean pore size ratings to commercial filters, which usually indicate meeting certain retention criteria for particles or microorganisms rather than the geometrical size of the actual pores.

In a particular embodiment the rotational cross flow filter element comprises a filter disc. In some embodiments the filter disc comprises a membrane with an average pore size of a microfilter. In other embodiments the filter disc comprises a membrane with an average pore size of an ultrafilter. In an embodiment the average pore size of the filter disc membrane is in a range from greater than or equal to 5 nm to less than or equal to 2 µm. In particular embodiments the average pore size of the filter disc membrane is in a range from greater than or equal to 50 nm to less than or equal to 0.5 µm. In some embodiments the filter disc membrane has an average pore size in the range of greater than or equal to 50 nm to less than or equal to 100 nm, or in the range of greater than or equal to 60 nm to less than or equal to 90 nm, or in the range of greater than or equal to 60 nm to less than or equal to 80 nm. In some embodiments the filter disc membrane has an average pore size of 60 nm or 80 nm.

In a preferred embodiment the rotational cross flow filter element comprises a filter disc comprising a ceramic membrane.

Ceramic filters can be for example composed of $Al_2O_3$, or $ZrO_3$, $TiO_2$ or $MgAl_2O_4$. Ceramic disc filters are typically designed so that filtrate is transported across the ceramic membrane from the outside into a hollow inner channel from which the filtrate can be collected.

Ceramic disc filters are available in various sizes including with outer diameters of 374 mm (surface area 0.2 $m^2$), 312 mm (surface area 0.14 $m^2$) and 152 mm (surface area 360 $cm^2$). Typically the ceramic disc filters have a thickness ranging from about 4.5 to 6 mm.

In embodiments of the present invention the ceramic filter disc has a membrane with an average pore size of a microfilter. In other embodiments the ceramic filter disc has a membrane with an average pore size of an ultrafilter. In certain embodiments the average pore size of the ceramic membrane is in a range from greater than or equal to 5 nm to less than or equal to 2 µm. In particular embodiments the ceramic membrane has a pore size from about 0.2 µm to 2 µm. In particular embodiments the ceramic membrane has an average pore size from about 5 nm to about 100 nm. In other embodiments the average pore size of the ceramic membrane is in a range from greater than or equal to 50 nm to less than or equal to 0.2 µm. In some embodiments the ceramic filter membrane has an average pore size in the range of greater than or equal to 50 nm to less than or equal to 100 nm, or in the range of greater than or equal to 60 nm to less than or equal to 90 nm. In a preferred embodiment the ceramic filter membrane has an average pore size in the range of greater than or equal to 60 nm to less than or equal to 80 nm. In another preferred embodiment the ceramic membrane has an average pore size of 60 nm. In another preferred embodiment the ceramic membrane disc has an average pore size of 80 nm.

According to yet a further preferred embodiment, a second filtration element comprises an ultrafiltration device comprising a membrane with an average molecular weight cutoff value of less than 50 kD, preferably less than 30 kD, more preferably less than 10 kD or most preferably less than 5 kD.

In embodiments of the invention the first process unit filter capacity is at least 25 kg or at least 50 kg or at least 75 kg or at least 100 kg or at least 200 kg or at least 300 kg or at least 350 kg or at least 400 kg or at least 450 kg or at least 500 kg or at least 550 kg or at least 600 kg or at least 650 kg or at least 700 kg or at least 750 kg or at least 1000 kg of the starting precipitate per m$^2$ of filter surface area.

DETAILED DESCRIPTION OF THE INVENTION

The present invention relates to a system and a method for maximising protein recovery and yield by using a novel first process unit or further with a second process unit. The combination of an extraction and separation method is used in the present invention to process a solid protein-comprising precipitate i.e. an intermediate material (e.g. paste derived from a starting material) wherein the precipitate maybe suspended in a liquid or diluent e.g. water or buffer, to form a suspension.

Typical protein containing precipitates are formed during the purification of proteins after exposure to precipitants such as ethanol. The solid is often called the precipitate or paste. The precipitate can be mixed with liquid to form a suspension in which solid particles are distributed throughout the liquid. Under particular extraction conditions the protein contained in these particles can be progressively dissolved into the liquid phase.

The dissolution ratio in industrial scaled manufacturing processes poses a problem because of the large volume of water or buffer required. For plasma fractionation processes used to manufacture proteins like albumin and immunoglobulins this step can involve many thousands of litres. Even when tanks are available to hold such large volumes to enable large dissolution ratios, the desired effect of higher yield can fail to materialize because of an equilibrium (Chatelier's principle) between protein dissolved in the solution and that remaining in the precipitate or paste. Such protein trapped in the precipitate may not be recoverable for further processing to final product. This phenomenon is related in part to the solubility equilibrium. As a known solubility equilibrium exists when a compound in the solid phase is in chemical equilibrium with the compound dissolved in the solution. The equilibrium is an example of a dynamic equilibrium in that some individual molecules migrate between the solid and liquid phases such that the rates of dissolution and precipitation are equal to one another.

This invention aims to solve the problem of protein recovery from precipitates by continuously shifting the solubility equilibrium. This is achieved by: 1) increasing the extraction efficiency (using dynamic filtration system which can incorporate hollow rotating disk filter elements) with built-in components to allow intimate phase contact in a repetitive way; 2) continuously removing dissolved protein from the protein containing precipitate (by applying Le Chatelier's principle—When any system at equilibrium is subjected to change in concentration (e.g. volume), temperature, or pressure, then the system re-adjusts to counteract (partially) the effect of the applied change and a new equilibrium is established. This means by continuously increasing the volume at the resuspension site and continuously removing the dissolved protein through the dynamic filter, Le Chatelier's principle can be utilized to ensure maximum protein transfer from the precipitate into the liquid phase. In some instances increased volume can be realized by recycling the permeate during a continuous concentration step of the protein, thereby reducing consumption of buffer.

Large or industrial scale with regard to the present invention represents production procedures based on at least 200 L, preferably at least 500 L, even more preferably at least 2000 L of a starting material such as human plasma. For example typical commercial plasma donor pool sizes used in industrial scaled protein manufacture range from 2500 L to 6000 L of plasma per batch. In particular embodiments of the invention the precipitate is obtained from 2500 L to 6000 L of plasma. Some commercial manufacturing processes are capable of using even larger plasma donor pool sizes including up to 7500 L, up to 10000 L, and/or up to 15000 L of plasma.

The method and system of the invention can also be used not only for large industrial scale applications but as a stand-alone system and/or method for smaller production scale applications (where the starting material may be less than 200 L).

Many different methods can be used to selectively precipitate proteins from solution, for instance by the addition of salts, alcohols and/or polyethylene glycol with the combination of pH adjustment and/or a cooling step. It is therefore anticipated that the present invention will be applicable to most protein precipitates, such as immunoglobulin G-containing protein precipitates, regardless of how they are initially prepared. It should be noted that the present invention can also be implemented in separating other types of protein including albumin, immunoglobulins (Ig), such as IgA, IgD, IgE or IgM, either each type of immunoglobulin alone or a mixture thereof. It is foreseen that recombinant proteins are also suitable in this regard.

To this end, it is noted that, if the method is applied to producing IgG, the protein-comprising precipitate can be any IgG-containing material (e.g. in form of a paste, precipitate, or inclusion bodies) or derived from a starting material such as a solution from which the IgG can be precipitated by for example one or more of the methods explained above, whether from plasma or serum of human or animal origin, fermentation broth, cell culture, protein suspension, milk or other original sources. The immunoglobulin-containing material or solution may contain monoclonal or polyclonal immunoglobulin(s). In some embodiments, the immunoglobulin-containing starting material is a solution comprising polyclonal antibodies. In other embodiments the starting material comprises a monoclonal antibody or a fragment thereof. It is therefore within the knowledge of a skilled person that the term "immunoglobulin" as used herein can also be identified as antibody including monoclonal antibody or polyclonal antibody, either natural or recombinant.

For instance, the immunoglobulins (e.g. IgG) can be isolated from human or animal blood or produced by other means such as by recombinant DNA technology or hybridoma technology. In preferred embodiments, immunoglobulins are obtained from blood plasma, typically from a pool of blood plasma derived from many donors. In order to obtain the immunoglobulins from plasma, the plasma is usually subjected to alcohol fractionation, which may be combined with other purification techniques like chromatography, adsorption or precipitation. However, other processes can also be used. For instance, the protein-comprising precipitate can be the II+III precipitate according to the Cohn's methods such as the Method 6, Cohn et. al. J. Am; Chem. Soc., 68 (3), 459-475 (1946), the Method 9, Oncley et al. J. Am; Chem. Soc., 71, 541-550 (1946), or the I+II+III precipitate, the Method 10, Cohn et. al. J. Am; Chem. Soc., 72, 465-474 (1950); as well as the Method of Deutsch et. al. J. Biol. Chem. 164, 109-118 (1946) or the Precipitate-A of Nitschmann and Kistler Vox Sang. 7, 414-424 (1962); Helv. Chim. Acta 37, 866-873 (1954). Alternative precipitates comprising the protein of interest include but are not limited to other immunoglobulin G-containing Oncley fractions, Cohn fractions, ammonium sulphate precipitates from plasma described by Schulze et al. in U.S. Pat. No. 3,301, 842. Further alternative precipitates comprising the protein of interest include but are not limited to octanoic acid precipitates, as described, for example, in EP893450.

"Normal plasma", "hyperimmune plasma" (such as hyperimmune anti-D, tetanus or hepatitis B plasma) or any plasma equivalent thereto can be used as a starting material in the cold ethanol fractionation processes described herein.

The term 'cryosupernatant' (also called cryo-poor plasma, cryoprecipitate depleted plasma and similar) refers to plasma (derived from either whole blood donations or plasmapheresis) from which the cryoprecipitate has been removed. Cryoprecipitation is the first step in most plasma protein fractionation methods in use today, for the large-scale production of plasma protein therapeutics. The method generally involves pooling frozen plasma that is thawed under controlled conditions (e.g. at or below 6° C.) and the precipitate is then collected by either filtration or centrifugation. The supernatant fraction, known to those skilled in the art as a "cryosupernatant", is generally retained for use. The resulting cryo-poor plasma has reduced levels of Factor VIII (FVIII), von Willebrand factor (VWF), Factor XIII (FXIII), fibronectin and fibrinogen. While the levels of FVIII are greatly reduced, levels of fibrinogen can be as much as 70% of original levels. Cryosupernatant provides a common feedstock used to manufacture a range of therapeutic proteins, including alpha 1-antitrypsin (AAT), apolipoprotein A-I (APO), fibrinogen, antithrombin III (ATM), prothrombin complex comprising the coagulation factors (II, VII, IX and X), albumin (ALB) and immunoglobulins such as immunoglobulin G (IgG).

The supernatant of the 8% ethanol-precipitate (method of Cohn et al.; Schultze et al. (see above), p. 251), precipitate II+III (method of Oncley et al.; Schultze et al. (see above) p. 253) or precipitate B (method of Kistler and Nitschmann; Schultze et al. (see Schultze above), p. 253) are examples of a source of IgG compatible with industrial scale plasma fractionation. The starting material for a purification process to gain IgG in high yield can alternatively be any other suitable material from different sources like fermentation and cell culture or other protein suspensions.

In the Cohn fractionation method, the first fractionation step results in fraction I which comprises mainly fibrinogen and fibronectin. The supernatant from this step is further processed to precipitate out fraction II+III and then fractions III and II. Typically, fraction II+III contains approximately 60% IgG, together with impurities such as fibrinogen, IgM, and IgA.

Most of these impurities are then removed in fraction III, which is considered a waste fraction and is normally discarded. The supernatant is then treated to precipitate out the main IgG-containing fraction, fraction II, which can contain greater than 90% IgG. The above % values refer to % purity of the IgG. Purity can be measured by any method known in the art, such as gel electrophoresis or immune-nephelometry. In the Kistler & Nitschmann method, fraction I is equivalent to fraction I of the Cohn method. The next precipitate/fraction is referred to as precipitate A (fraction A). This precipitate is broadly equivalent, although not identical, to Cohn fraction II+III. The precipitate is then redissolved and conditions adjusted to precipitate out precipitate B (fraction B), which is equivalent to Cohn fraction III. Again, this is considered to be a waste fraction, and is normally discarded. The precipitate B supernatant is then processed further to produce precipitate II, which corresponds to Cohn Fraction II.

Particular protein-comprising precipitates can comprise plasma proteins, peptide hormones, growth factors, cytokines and polyclonal immunoglobulins proteins, plasma proteins selected from human and animal blood clotting factors including fibrinogen, prothrombin, thrombin, prothrombin complex, FX, FXa, FIX, FIXa, FVII, FVIIa, FXI, FXIa, FXII, FXIIa, FXIII and FXIIIa, von Willebrand factor, transport proteins including albumin, transferrin, ceruloplasmin, haptoglobin, hemoglobulin and hemopexin, protease inhibitors including $\beta$-antithrombin, $\alpha$-antithrombin, $\alpha$-2-macroglobulin, C1-inhibitor, tissue factor pathway inhibitor (TFPI), heparin cofactor II, protein C inhibitor (PAI-3), Protein C and Protein S, $\alpha$-1 esterase inhibitor proteins, $\alpha$-1 antitrypsin, antiangionetic proteins including latent-antithrombin, highly glycosylated proteins including $\alpha$-1-acid glycoprotein, antichymotrypsin, inter-$\alpha$-trypsin inhibitor, $\alpha$-2-HS glycoprotein and C-reactive protein and other proteins including histidine-rich glycoprotein, mannan binding lectin, C4-binding protein, fibronectin, GC-globulin, plasminogen, blood factors such as erythropoietin, interferon, tumor factors, tPA, $\gamma$CSF.

In particular embodiments the protein-comprising precipitate is used in the manufacture of therapeutic proteins derived from plasma including immunoglobulins such as immunoglobuilin G, albumin, fibrin, thrombin, prothrombin complex, fibrinogen, plasminogen, alpha 1-antitrypsin, C1-inhibitor, apolipoprotein A1, alpha acid glycoprotein, haptoglobin, hemopexin, transferrin and coagulation factors such as Factor VII, Factor VIII and Factor IX.

The concentration of protein(s) in a sample (e.g., in the supernatant or a subsequently purified preparation thereof) can be measured by any means known to persons skilled in the art. Examples of suitable assays include high pressure liquid chromatography (HPLC; e.g., size exclusion HPLC), enzyme-linked immunosorbent assay (ELISA) and immunonephelometry.

Such techniques can be used to assess purity of a sample. In addition gel electrophoresis like SDS-PAGE with staining and densitometry may be used to assess purity of the sample and detect the presence of contaminating proteins. A reducing agent such as dithiothreitol can be used with SDS-PAGE to cleave any disulfide-linked polymers.

The immunoglobulin G-containing starting material preferably has a total protein concentration of about 0.5 to 6.5% w/v, more preferably about 1.0 to 4.0% w/v, still more preferably about 1.5 to 3.0% w/v, most preferably about 1.8 to 2.5% w/v, e.g. about 2.0% w/v.

In one embodiment the liquid comprises a buffer comprising one of more of sodium acetate, phosphate and citric acid. In one embodiment the phosphate is a sodium phosphate, such as sodium dihydrogen phosphate dehydrate. Preferably, a buffer with low conductivity is used, such as a buffer with a conductivity below 5 mS/cm, preferably below 4 mS/cm, more preferably between 0.01 mS/cm to 4 mS/cm.

The method according to the present invention allows the protein of interest to be recovered in high yield from the protein-comprising precipitate (e.g. paste). The recovered yield (ultrafiltrated product), in post concentration stage, is typically at least 95% (w/w), preferably at least 96% (w/w), more preferably at least 97% (w/w), most preferably up to 98% (w/w), which is defined as the total amount of immunoglobulin G in the final filtrated solution compared to the total amount of immunoglobulin G in the starting material.

The following is an example demonstrating how the calculation of the recovery rate of the immunoglobulin G content can be obtained according to the present invention. A first step involves the determination of the IgG content in the protein-comprising precipitate (total dissolution) followed by a second step which involves the determination of the IgG recovery using the continuous extraction method or system of the present invention.

As a first step, the protein-comprising precipitate (about 50 g for each experiment) is dissolved in a buffer (e.g., 0.12 M to 0.25 M phosphate buffer, pH 7.6 to 8.0) to give a final dilution factor of 20 (1:20; or a final dilution ratio of 1:19 by weight). After a resuspension duration of 2 h using an impeller mixer, the suspension is centrifuged at 4500 G. This results in a first supernatant and a first precipitate. The volume of supernatant can be determined by standard methods, and the IgG content of the supernatant can be determined, for example, by nephelometry. The resulting precipitate is resuspended and treated again using the same buffer as described above to give a final dilution factor of 20 (1 part of supernatant obtained:19 parts of new buffer). The volume of the resulting supernatant and IgG content is determined again. This process is repeated for example five times, or as often as necessary so that the IgG content in the last supernatant is below 10 mg/L (quantification limit is approximately about 3.6 mg/L). This procedure ensures that the IgG content in the protein-comprising precipitate is completely or optimally dissolved or extracted by the buffer. This experiment is repeated several times (12 individual experiments were repeated in the present case). This process was repeated with different starting precipitates generated from fractionation of source plasma which gave similar reliable results. Table 1 below shows the content of the total protein and IgG recovered from the protein-comprising precipitate.

TABLE 1

Determination of the IgG content in the protein-comprising precipitate (total dissolution).

| | accumulative dilution factor (paste:buffer) weight:weight | Recovery total protein (g/kg paste) (min-max) | Recovery IgG (g/kg paste) (min-max) |
|---|---|---|---|
| After 1. extraction | 1:20 | 131.8-158.9 | 68.7-72.8 |
| After 2. extraction | 1:40 | 16.2-23.1 | 7.1-10.5 |
| After 3. extraction | 1:60 | 3.5-7.4 | 0.6-1.8 |
| After 4. extraction | 1:80 | 1.1-2.3 | 0.05-0.2 |

TABLE 1-continued

Determination of the IgG content in the protein-comprising precipitate (total dissolution).

| | accumulative dilution factor (paste:buffer) weight:weight | Recovery total protein (g/kg paste) (min-max) | Recovery IgG (g/kg paste) (min-max) |
|---|---|---|---|
| After 5. extraction | 1:100 | 0.2-0.4 | 0.01-0.03 |
| Total extraction | | 152.8-192.1 | 76.5-85.3 |

In the second step, the same protein-comprising precipitate is used for the experiment with the continuous extraction and separation method or system according to the present invention. A total amount of 1 kg of the protein-comprising precipitate (Precipitate A) is dissolved in the buffer (e.g. 10 mM phosphate, 10 mM acetate & 2 mM citric acid) for 30 minutes to give a starting suspension with a first dilution ratio of 5 (1:6 by weight; or equal to a first dilution factor of 6 (1:6)). The pH of the suspension is 4.6. The suspension is transferred from a first tank into a first filtration process unit for a continuous extraction and separation process. The filtrate (first permeate) is collected in a second tank. For each 100 to 200 ml collected filtrate, 100 to 200 ml of fresh buffer (or recirculated buffer (i.e. second permeate) after the UF step) is added to the first tank such that the volume of the filtrated suspension remains constant in the first tank. The filtration is terminated after 4 hours, whereby the total protein concentration in the suspension is expected to be below 0.1 g/L and/or the IgG concentration is below 50 mg/L. The following Table 2 shows the recovery rate of the IgG.

TABLE 2

Determination of the IgG recovery using the continuous extraction filtration system of the present invention

| Starting precipitate used | Precipitate A |
|---|---|
| Amount of starting precipitate (kg) | 1.0 |
| First dilution factor (paste:total by weight) | 1:6 |
| Total protein amount (at the first dilution factor) (g/kg paste) | 116.4 |
| IgG amount (at the first dilution factor) (g/kg paste) | 61.7 |
| Final dilution factor (end of the continuous extraction & filtration) | 1:31 |
| Total protein amount (after reaching the final dilution factor) (g/kg paste) | 168 |
| IgG amount (after reaching the final dilution factor) (g/kg paste) | 78.9 |
| IgG amount (post ultra-filtration) (g/kg paste) | 78.6 |

In this example, the experiment is performed off-line to show the increased yield of total protein and IgG using the continuous extraction filtration unit. "Off-line" means that the buffer added is not obtained from a second filtration unit. Ultrafiltration in the second filtration unit is carried out separately. Also it is shown in Table 2 that the IgG amount is lower at the first dilution factor (1:6=61.7 g/kg) compared to the IgG amount at the end of the final (second) dilution factor (1:31=78.9 g/kg). This is due to the fact that not all IgG is extracted or dissolved in the buffer at once but rather is extracted or dissolved over a period or a repetitive dissolving procedure. Hence, the IgG yield is increased through the continuous extraction and filtration process according to the present invention.

The yield of the immunoglobulin G according to the present invention with a recovery rate of at least 95% is achieved, as shown by Tables 1 and 2 above. The recovery rate (of the continuous extraction and filtration according to the present invention) is calculated by the ratio (of total amount of IgG in continuous filtrate:average amount of IgG by total dissolution from Table 1) multiplied by 100.

Total IgG amount (after reaching the final dilution factor)=78.9 g/kg

Average total IgG extraction (Table 1)=(76.5+85.3)/2=80.9 g/kg

Yield of IgG (Recovery rate)=78.9/80.9× 100%=97.53%

Hence, it is shown herewith that at least 95% or approximately 98% of IgG recovery rate according to the present invention can be achieved.

High recovery at this early process step (before further downstream processing steps) is a prerequisite to achieve higher yields at the final bulk stage. The present invention utilizes the extraction process, wherein protein-comprising precipitate (e.g. paste) is in effect suspended with a high dilution factor (e.g. between 40 and 70; 1:40 and 1:70). As an example, 1 kg of protein-comprising precipitate (e.g. paste) is resuspended in 3 kg of liquid (e.g. buffer), resulting in a starting suspension with a first dilution factor of 4 (1:4). Recirculation of 66 kg of the feedstream of buffer results in a final dilution factor of 70 (1:70). The extraction process used in the present invention allows higher amounts of immunoglobulin G to be released into the suspension/solution, thus shifting the equilibrium (as will be discussed below), allowing for a more efficient separation of immunoglobulin G from the suspension.

In a preferred embodiment, the crude immunoglobulin G-containing protein precipitate (i.e. the protein-comprising precipitate) is suspended in a buffer to yield the starting suspension. The buffer may in some embodiments contain acetate or phosphate, or additionally citric acid.

In the most preferred embodiment, the extracted and filtrated product of immunoglobulin G enriched suspension or solution comprises human immunoglobulin, wherein at least 95% or up to 98% immunoglobulin G content is recovered from the starting precipitate, or less than 0.1 mg/ml, preferably less than 0.05 mg/ml of immunoglobulin G protein concentration can be detected in final suspension after the second dilution factor has been reached. The approximate distribution of the immunoglobulin G subclasses will typically resemble about the average subclass distribution in human plasma.

Moreover, typically 1 kg of Precipitate A (protein-comprising precipitate) contains around 170 g of total protein (range: 150-190 g protein/kg precipitate). The total protein is made up of approximately 50% to 60% of IgG (thus ranging between 75-95 g/kg precipitate). According to the one method of the present invention, when a recovery rate of approximately 98% of IgG is achieved, that means a total amount of 73.5-93.1 g/kg of IgG are obtained from the protein-comprising precipitate (Precipitate A).

As will be illustrated in detail in the examples hereinafter, due to the improved extraction process for extracting immunoglobulin G disclosed in the present method, in which the improved method is comprised of treating the paste (i.e. protein-comprising precipitate/material) with a larger volume of buffer, regardless of the pH of the buffer, a surprisingly high recovery rate of approximately 98% of the immunoglobulin G can be obtained. It is presently common in the art to use a lower final dilution factor (e.g. from 5 and up to between 14 to 15). For example, in WO2016012803 the weight of waste fraction to solvent will generally be from about 1:2 to about 1:10. Preferably, the weight of solvent may be approximately four times the weight of the waste fraction, i.e. a weight ratio of about 1:4 of waste fraction to solvent. Hence, the present invention enables improved recoveries by providing a means to expose the immunoglobulin comprising precipitate to a higher volume (high final dilution factor of 20, 30, 40 or higher). Additional factors that also contribute include the introduction of turbulences in the suspension, a pressure of up to 2 bar in the first and/or second process units as well as the closed filtration system according to the present invention has increased the extraction efficiency, leading to a high recovery rate of immunoglobulin G extracted from the starting precipitate. Moreover, apart from the unexpectedly high recovery yield, the present invention also offers other advantages, in particular scalability, whereby it allows the method of the invention to be used in the existing facilities due to smaller footprints, and lower costs associated with handling lower total volumes; in addition, it still allows controllability of parameters which could affect the quality and stability of the immunoglobulin G. Finally the use of a dynamic filtration enables high solid content suspensions to be effectively filtered.

In chemistry for instance in protein separation, Le Chatelier's principle or "The Equilibrium Law" can be used to predict the effect of a change in conditions on a chemical equilibrium. When any system at equilibrium is subjected to change in concentration, temperature, volume, or pressure, then the system readjusts itself to counteract (partially) the effect of the applied change and a new equilibrium is established. In other words, whenever a system in equilibrium is disturbed the system will adjust itself in such a way that the effect of the change will be nullified. For instance, at equilibrium, the concentrations of immunoglobulin in suspension on either side are constant. If at equilibrium a small amount of the immunoglobulin is taken out from the reaction, due to the changing of the immunoglobulin concentration, this will shift the equilibrium to the side that would reduce that change in concentration. According to Le Chatelier's principle the system will attempt to partially oppose the change affected to the original state of equilibrium. In turn, the rate of reaction, extent and yield of products will be altered corresponding to the impact on the system.

If a system is at equilibrium and the concentration of one of the species involved in the reaction is increased, the system will readjust so as to decrease the concentration of that species. Thus, the reaction will proceed in such a manner so as to consume some of the increased concentration. Similarly if the concentration of some substance is decreased, the reaction will proceed so as to make up the loss in the concentration.

In other words, under constant removal of immunoglobulin (e.g. IgG) from the system and at the same time, reducing the concentration of immunoglobulin in the solvent of the suspension through dilution, this leads to the increase of removing immunoglobulin from one phase of the suspension, i.e. the precipitate to the liquid phase. Through repetition of this procedure essentially all immunoglobulin included in the precipitate of the suspension can be extracted from the protein-comprising precipitate, in particular present invention discloses a high final dilution factor of at least 30, preferably e.g. 40 (1:40) or higher, and can be further assisted by using for example the proposed buffer compositions, or additionally assisted by using a higher pH to maximise immunoglobulin G recovery from the protein-comprising precipitate. Compared to the prior art, the method and system of the present invention allows almost all immunoglobulin G to be recovered from the protein-comprising precipitate (e.g. paste or precipitate).

The ultrafiltrated product can later be subjected to further processing such as chromatography steps, virus inactivation steps, concentration and formulation so that the end product can be administered for example to the human body. The end product can be used in the treatment of immune conditions, particular autoimmune diseases and certain neurological diseases. These conditions include Rheumatoid arthritis, Systemic Lupus Erythematosus (SLE), Antiphospholipid syndrome, immune thrombocytopenia (ITP), Kawasaki disease, Guillain Barre syndrome (GBS), multiple sclerosis (MS), chronic inflammatory demyelinating polyneuropathy (CIDP), multifocal motor neuropathy (MMN), myasthenia gravis (MG), skin blistering diseases, scleroderma, Dermatomyositis, Polymyositis, Alzheimer's Disease, Parkinson's Disease, Alzheimer's Disease related to Downs Syndrome, cerebral amyloid angiopathy, Dementia with Lewy bodies, Fronto-temporal lobar degeneration or vascular dementia. In addition the end IVIG and SCIG products can be used in other medical procedures such as in cell and organ transplant.

To this end, it is reiterated that the first process unit according to the present invention provides a continuous extraction and separation process, in particular a filtration process, thanks to its unique design. The first process unit may be provided with a dynamic rotation filtration element, for example comprising a ceramic-based membrane disc. The rotation filtration allows extreme cross flow velocity (due to its high efficient cleaning of the filter surface) and has a very low energy consumption compared to conventional cross flow techniques. A cross flow effect (tangentially flow cleaning of the filter surface) is generated by the rotating of the filter discs and not by pumping of large volumes. The ceramic filter disc has better resistance to chemical and thermal stresses, high filtration flux and very long service life, and can be regenerated by backflushing or hot steam sterilization.

Rotating Ceramic Filter Discs are typically assembled in a pressurised housing. The design of the discs shows drainage channels in the inside. The filtrate is transported from the outside to the inside of the discs. The rotation of the discs generates shear forces on the membrane surface. With this technique an increase of a filter cake is avoided resulting in a high filtration flux. Some of main parameters of the rotation filtration is the rotation speed for rotating the ceramic filter disc and solid content (concentration of liquids due to the removal of filtrate).

The term "protein-comprising precipitate" is intended to refer to any material containing the protein of interest. In the context of immunoglobulin as the protein of interest, this term may refer to plasma, serum, precipitates produced from plasma or serum, fermentation broths, inclusion bodies, cell culture supernatants, or precipitates produced from such materials. Typically, in the context of the present invention, it refers to precipitates from plasma, such as Cohn or Oncley ethanol precipitates, or Kistler-Nitschmann precipitates.

The term "starting composition" refers to a suspension or solution, produced from the protein-comprising precipitate, typically by dilution with water or buffer according to a (first) dilution factor. In some instances, if no dilution of the protein-comprising precipitate is required, the protein-comprising precipitate may be the starting suspension.

By "high yield" it is meant that the yield of the protein of interest such as immunoglobulin G (as well as other proteins and immunoglobulins) is at least 95% of the amount of the protein of interest in the protein-comprising precipitate, preferably at least 96%, more preferably at least 98%, most preferably more than 98%.

The concentration of immunoglobulin in a sample (e.g., in the precipitate or in a pharmaceutical-grade purified preparation thereof) can be measured by any means known to persons skilled in the art. It will be understood that the method used to measure immunoglobulin may depend on the nature of the sample. For example, it will be understood that, where the sample is an immunoglobulin-containing precipitate, it may be necessary to dissolve the precipitate (or a sample thereof) in a suitable buffer prior to the measurement. Examples of suitable assays for measuring a protein of interest include high pressure liquid chromatography (HPLC; e.g., size exclusion HPLC), enzyme-linked immunosorbent assay (ELISA) and quantitative immunonephelometry.

By "about" or "approximately" in relation to a given numerical value for percentage, pH, amount or a period of time or other references, it is meant to include numerical values within 10% of the specified value.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

It must be noted that, as used in the subject specification, the singular forms "a", "an" and "the" include plural aspects unless the context clearly dictates otherwise. Thus, for example, reference to "a protein" includes a single protein, as well as two or more proteins.

Several preferred embodiments of the present invention will now be described in detail with reference to the accompanying figure, wherein some of the less or non-essential features of the figure incorporated herein have been omitted for conciseness.

BRIEF DESCRIPTION OF THE DRAWINGS

The following drawings are not necessarily drawn to scale, emphasis instead is generally being placed upon illustrating the principles of various embodiments. In the following description, various embodiments of the invention are described with reference to the following drawing:

FIG. 1 illustrates a schematic flow chart overview of the system 100 and the method according to one preferred embodiment of the present invention. Protein-comprising precipitate e.g. in form of a suspension, or in form of a paste or precipitate is suspended with liquid e.g. buffer. The compositions and concentration of the buffer are in accordance with the above described method in order to generate a starting composition such as a suspension having a first dilution factor e.g. between 3 to 10 (1:3 to 1:10). The suspension is housed in a first tank 1. The suspension can be fed to a first filtration unit 5, through the pump 2, several type of pumps can be used (e.g. piston-; rotary-; centrifugal- and membrane pump) and flow-regulated valve 3 of a pipe 12. The first filtration unit 5 is equipped with a rotating hollow shaft to which the filter discs are mounted (the filtrate flows from the outside to the inside of hollow shaft). The first filtration unit 5 is further set up with height adjustable scrapers to keep the filter cake thickness constant and thus achieve constant filtrate flow. The desired filtration pressure is controlled and regulated by overflow valve (unfiltered suspension outlet). The filter discs used can be a ceramic membrane, depth filter layers and sintered porous metal filter discs. Once the vessel of the first filtration unit 5 is filled with the suspension, a continuous pressure extraction and separation can be started. The first filtration unit 5, which can comprise a pressure unit/vessel, is provided with suitable internal settings and conditions to simultaneously increase the extraction efficiency and filtration process. The extraction efficiency is increased through turbulence mixing in the unit 5 without having to involve a mixer. Nevertheless, it can be foreseen that an additional mixer may be provided to assist the extraction process by creating turbulences. Moreover, higher final dilution factor e.g. 40 or 70 disclosed in the present invention also increases the extraction efficiency, leading to high protein (e.g. IgG) yield. Of course, any other higher final dilution factor (higher than 70) can also be envisaged.

Figure 1:
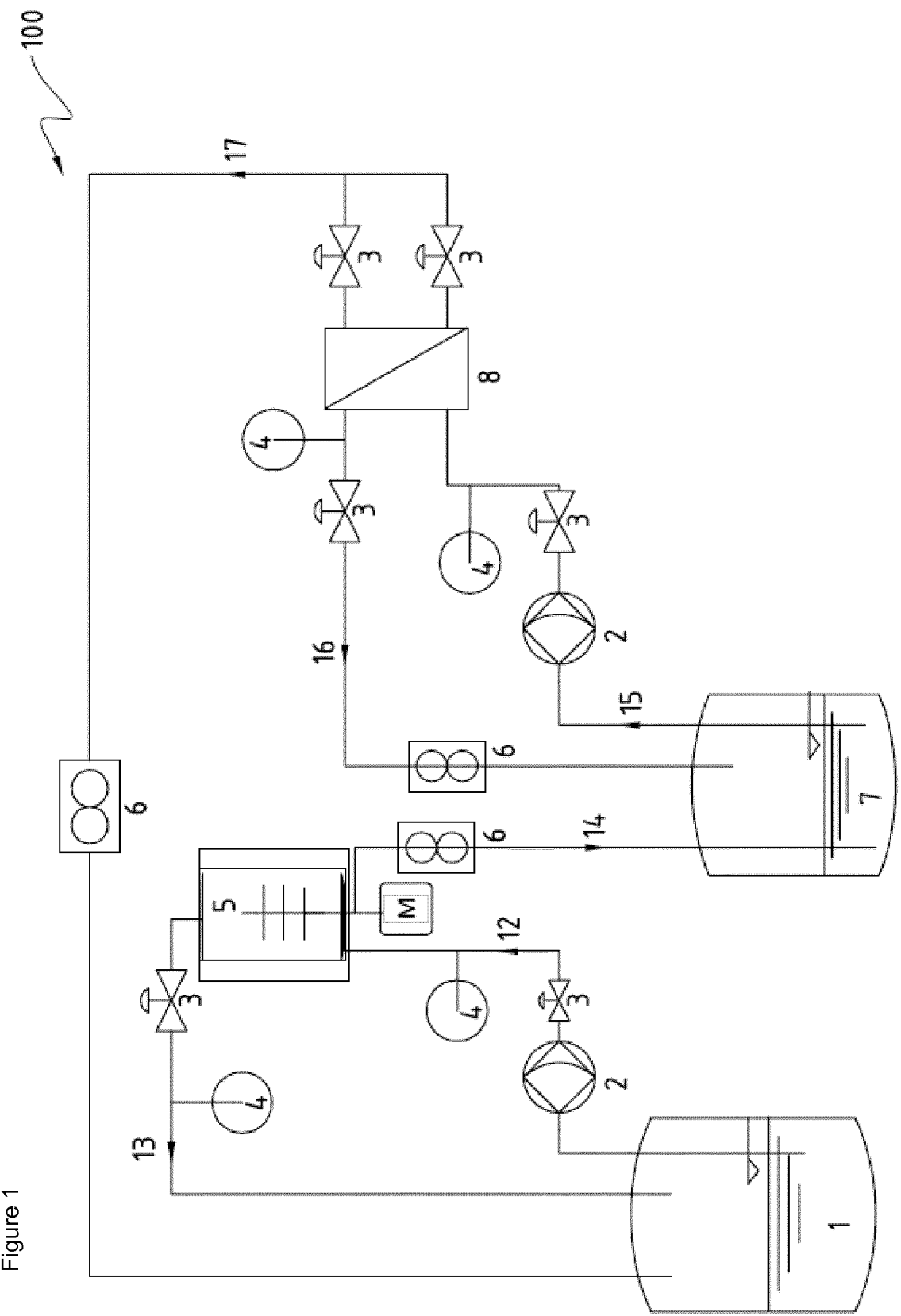
FIG. 1 is a schematic flow chart overview of the system of the present invention, and is described in more detail below.

The filtrate flows through a flowmeter 6 installed on pipe (or channel) 14 and is collected in the second tank 7. The unfiltered suspension flows back through the regulated outlet 3 installed on pipe 13 in tank 1. When a defined volume in the second tank 7 is reached, the UF 8 concentration process can be started in the second filtration unit. The filtrate in the second tank 7 flows through pipe 15 into the ultrafiltration (UF) system 8. The transmembrane pressure is set such that the permeate flow rate 17 is identical or almost identical to that with the first filtrate flow rate in pipe 14. The permeate of the UF system 8 flows through pipe (or line or channel) 17 back to the first tank 1, whereas the retentate of the UF system (=concentrated protein) flows through pipe 16 back to the second tank 7.

In accordance with the invention, the first process unit 5 is provided with one or more rotating filter discs comprising one or more of the first filter element for turbulence mixing of the content of the first process unit 5 for producing the first retentate and the first permeate. The first retentate can be fed back to the first tank 1 through a channel 13 via a control valve 3 whereas the first permeate can be fed to a second tank 7 via another channel 14. The first filter element can be a filtration membrane which is based on a ceramic material, having a pore diameter of between about 5 nm to 5000 nm, preferably between 20 nm to 100 nm or more preferably between 30 nm to 80 nm. It can also be foreseen that inorganic membranes or any other suitable membranes could also provide a similar effect as the ceramic based membrane. The first filtration unit 5 may be supplied with a pressure control device 4 such as a manometer in order to regulate the pressure within. Similarly, a flowmeter 6 can be installed in the system of the present invention for measuring the flow rate of the suspension or solution.

Feedstream from the second tank 7 can then be fed to a second filtration unit 8 through a channel 15 for a second separation process to be carried out. The second separation process can be a continuous concentration process (e.g. UF). The second filtration unit 8 is provided with one or more second cross flow filter element/s, wherein the second cross flow filter element can comprise an ultrafiltration membrane having an average molecular weight cutoff value of less than 50 kD. However, the membrane can also be less than 10 kD or more preferably less than 5 kD. The ultrafiltration membrane therefore produces a second retentate which is channeled back to the second tank 7 through a channel 16 whereas the second permeate is fed to the first tank 1 via a channel 17. To this end, it is noted that the pressure of the second filtration unit 10 can be regulated during concentration step (ultrafiltration) such that the flow velocity of channels 14 and 17 are substantially equal.

In the following description, a detailed description of the methods according to the present invention are outlined in several experimental examples.

Example 1

According to the present invention, immunoglobulin G was extracted through a continuous extraction and separation process in a first process unit.

An amount of 1 kg protein-comprising precipitate (Precipitate A) was dissolved in 10 mM sodium acetate, 10 mM phosphate and 2 mM citric acid buffer for 30 minutes to give a first dilution factor of 10 (i.e. 1 kg of the precipitate dissolved in 9 kg of buffer), wherein the pH of the suspension was about pH 4.6. The suspension was prepared in the first tank and was fed to the first process unit for a continuous extraction and separation process. The first process unit was provided with a rotation filtration element comprising a ceramic-based membrane disc, having a filtration membrane with an average pore size of 80 nm. The ceramic filter used was a Ceramic Filter Disc 152 which had a diameter Øo 152 mm/Øi 25.5 mm; thickness d=4.5 mm; and membrane surface area 360 cm$^2$. The tangential velocity of the disc was approximately 7 m/s at 60 Hz (800 rpm). The average filtration rate was about 200 ml/min. During the continuous extraction and separation process, for each 200 ml filtrate (first permeate) collected in a second tank, 200 ml of buffer was returned to the first tank from a second permeate obtained from a second filtration unit (ultrafiltration). After 4 hours the filtration was stopped, wherein the predetermined protein concentration in the first tank was less than 0.1 g/L (equates to a final dilution factor of 31). A total amount of 3 kg of the filtrate was further concentrated (10 kD ultrafilter membrane) in the second filtration unit to 20 g/L.

A comparative experiment was performed according to a prior art method using depth flow filtration. The same lot of Precipitate A was used in this experiment, wherein the precipitate was suspended in 0.22 M sodium acetate buffer. A final dilution factor of 6 (i.e. 1 kg of the precipitate dissolved in 5 kg of buffer) was used for this experiment. The suspension was mixed for 4 hours prior to depth filtration. Finally, the filtrate was concentrated to 20 g/L, using an ultrafiltration membrane having an average molecular weight cutoff of 10 kD.

The results of the immunoglobulin G yield are shown in Table 3. The IgG yield obtained using the continuous extraction method was higher than the prior art method. As explained above, the extraction method ensures the precipitate is exposed to an increased volume of liquid (or final dilution factor). This is thought to shift the dissolution equilibrium in favour of increased extraction of immunoglobulin G from the precipitate material which could then be recovered in the first permeate of the first filtration unit. As shown in Table 3, the dynamic filtration system of the present invention enabled an increase in IgG yield of approximately 0.68 g/L plasma equivalent (PEQ) compared to the prior art method. This equates to about 10% of the IgG in each liter of pooled plasma.

TABLE 3

Comparison of IgG yield between current and new process at different process steps.

|  | Control (prior art process) | Present invention (new process) |
| --- | --- | --- |
| First dilution factor | 6 (1:6) | 10 (1:10) |
| Resuspension time (h) | 2-8 | 0.5 |
| IgG yield (g/L PEQ) in Starting composition (suspension) | 5.86 | 5.80 |
| Final dilution factor | 6 (1:6) | 31 (1:31) |
| Filtrate | 5.53 | Not applicable |
| IgG yield (g/L PEQ) post continuous extraction and separation | Not applicable | 6.20 |
| IgG yield (g/L PEQ) post Ultra-concentration | 5.48 | 6.16 |

(PEQ stands for plasma equivalent i.e. the amount of IgG from each liter of plasma)

Example 2

In this example, IgG yields resulting from the use of different buffer compositions and different final dilution factors were compared using similar methods and equipment as described in Example 1.

As shown in Table 4, a final dilution factor of 6 was applied to the control (Sample A). This final dilution factor represents a common final dilution factor widely practiced in the art. For example, WO2016012803 (p. 15, line 30) suggests diluting by factors from about 1:2 to about 1:10. In contrast, the present invention provides a practical means to allow higher dilution ratios to be used. In the present example a final dilution factor of 40 was used for Samples B and C.

Buffer in Sample A comprises 0.22 M sodium acetate. Buffer in the Sample B comprises 5 mM acetate and 5 mM phosphate whereas the buffer in Sample C comprises 10 mM acetate and 10 mM phosphate. Both Samples B and C contained additionally 2 mM citric acid to maintain a constant pH after resuspension of the protein comprising precipitate. The pH of the starting composition in form of a suspension of all samples was approximately 4.8.

The final dilution factor for sample A of 6 was obtained by firstly dissolving approximately 1 kg of Precipitate I+II+III according to Cohn Method 10 in the buffer described above (0.22 M acetate; one part of precipitate and 5 parts of buffer; 1:6 wt/wt; precipitate:total). The suspension was mixed for 4 hours at an ambient room temperature. Thereafter, the suspension was filtered through a depth filter (0.2 to 0.45 µm, polypropylene), and finally ultra-concentrated through 10 kD membrane (Pellicon® 3) to 20 g protein/L.

A total amount of 1 kg protein-comprising precipitate was dissolved for Sample B as well as for Sample C in the above described buffer for 30 min to give a first dilution factor of 6, wherein the pH of the suspension was adjusted to about 4.6. The suspension was prepared in the first tank and was fed to the first process unit for a continuous extraction process. During the continuous extraction process, for each 100 to 200 ml filtrate collected in a second tank, 100 to 200 ml of buffer were returned to the first tank from the second permeate of the second process unit (ultrafiltration). The filtration process was stopped when the total dilution factor was about 40. The filtrate was further concentrated to 20 g/L in the second filtration unit using an ultrafiltration membrane having an average molecular weight cutoff value of 10 kD.

Six different lots were used for the experiments (comparing the same lot with each test buffer, respectively). The protein and immunoglobulin G yields were then compared. The yield results showed increases of 0.56 g immunoglobulin G per L PEQ (average) for both Samples B and C compared to Sample A (see Table 4).

TABLE 4

Comparison between prior art method (control) and methods used in the present invention post ultrafiltration concentration step.

|  | Control (prior art) | Present invention (proposed method) | |
| --- | --- | --- | --- |
|  |  | Sample | |
|  | A | B | C |
|  |  | Buffer | |
|  | Acetate (0.22M) | Acetate & Phosphate (5 mM; 5 mM) | Acetate & Phosphate (10 mM; 10 mM) |
| First dilution factor | 6 (1:6) | 6 (1:6) | 6 (1:6) |
| Final dilution factor | 6 (1:6) | 40 (1:40) | 40 (1:40) |
| IgG yield (g/L PEG) | 4.38 ± 0.24 | 4.89 ± 0.18 | 5.04 ± 0.14 |

Example 3

The impact of a different pH on the yield of immunoglobulin G, M and A and other impurities using the continuous extraction system of the present invention are demonstrated in this example. Two experiments were performed wherein IgG recoveries were compared using a citric acid buffer and a phosphate buffer. The protein-comprising precipitate used in this example was 1 kg Precipitate I+II+III derived from plasma treated with ethanol according to the Cohn Method 10 or according to the Kistler and Nitschmann method (1962, Vox Sang. 7, 414).

The lower pH sample was obtained by resuspending the above-described precipitate in a citric acid buffer (natrium citrate-citric acid) in order to give a first dilution factor of 5 (1:5) at a pH of 3.5 to 3.9. The suspension was stirred at 20° C. for 30 minutes.

The suspension was then transferred to the first tank which was subsequently fed to the first filtration process unit for a continuous extraction and separation process as described in Example 1. The first process unit was started as soon as the system was filled with the suspension. A first permeate/extract was produced from the first process unit, wherein the first permeate/first extract was collected in a second tank before it underwent an ultra-concentration step (second filtration unit). A second permeate depleted in the protein of interest obtained from the ultra-concentration step was fed back to the first tank. The continuous extraction and filtration process was stopped when the protein concentration in the first tank was less than 0.05 g/L and/or the final dilution factor was 40 (1:40).

The higher pH sample was obtained by resuspending the above-described precipitate in a phosphate buffer (disodium hydrogen phosphate $Na_2HPO_4$ and sodium dihydrogen phosphate NaH$_2$PO$_4$) in order to give a first dilution factor of 5 (1:5), and a pH of 8.0. The suspension was stirred at 20° C. for 30 minutes. Apart from the pH value, all other conditions and steps used in the higher pH sample were identical to low pH suspension (as described above).

Tables 5 and 6 show the results after the suspension had undergone the ultra-concentration step in the second filtration unit.

TABLE 5

IgG, IgA and IgM yield at ultra-concentrated step.

|  | Citrate | Phosphate |
|---|---|---|
| pH | 3.7 | 8.0 |
| IgG (g/L PEQ) | 6.38 | 6.42 |
| IgA (g/L PEQ) | 0.79 | 0.81 |
| IgM (g/L PEQ) | 0.48 | 0.50 |

The results demonstrate that the pH extraction conditions did not affect IgG, IgA or IgM yield. There were however effects observed in respect to other parameters with for example the low pH buffer conditions resulting in preparations with reduced levels of PKA and proteolytic activity. Such parameters can have a negative impact on the stability/quality of an immunoglobulin preparation. The parameters α1-Antitrypsin, α2-Macroglobulin, Transferrin, Albumin, Apo-AI, Ceruloplasmin, Haptoglobin, Fibrinogen, Fibronectin, Hemopexin and IgG-subclass distribution were determined by immunonephelometry assays. Phospholipid, triglyceride and cholesterol levels were determined by enzymatic test assays. Protein composition was performed by agarose gel electrophoresis. Molecular size distribution (Aggregate, Dimer, Monomer and Fragment) was determined by size exclusion chromatography. Determination of PKA and proteolytic activity were performed by chromogenic substrate assays.

TABLE 6

Impurity profile after ultra-concentration step

| Impurities | Citrate buffer [g/L] | Phosphate buffer [g/L] |
|---|---|---|
| Alpha1-Antitrypsin | 0.0931 | 0.0633 |
| Alpha2-Macroglobulin | 0.972 | 0.703 |
| Transferrin | 0.215 | 0.203 |
| Albumin | 1.32 | 1.29 |
| Apo-AI | 0.149 | 0.106 |
| Ceruloplasmin | 0.205 | 0.104 |
| Haptoglobin | 0.0763 | <0.07 |
| Fibrinogen | 1.16 | 1.79 |
| Fibronectin | 0.052 | 0.030 |
| Hemopexin | 0.0617 | <0.05 |
| Phospholipid | 0.2 | 0.25 |
| Triglyceride | 0.14 | 0.19 |
| Cholesterol | 0.19 | 0.28 |
| Protein composition | Percentage (%) |  |
| Albumin | 8.1 | 8.07 |
| Alpha-/Beta-Globulin | 16.8 | 23.9 |
| Gamma-Globulin | 75.1 | 68.1 |
| Molecular size distribution | Percentage (%) |  |
| Aggregate | 28.5 | 29.8 |
| Dimer | 6.5 | 6.5 |
| Monomer | 64.9 | 60.0 |
| Fragment | <0.1 | 3.7 |
| IgG-subclass | Percentage (%) |  |
| IgG1 [%] | 62.1 | 61.4 |
| IgG2 [%] | 27.9 | 30.3 |
| IgG3 [%] | 3.7 | 3.1 |
| IgG4 [%] | 6.3 | 5.2 |
| Other parameter |  |  |

TABLE 6-continued

Impurity profile after ultra-concentration step

| Impurities | Citrate buffer [g/L] | Phosphate buffer [g/L] |
|---|---|---|
| PKA [IU/mL] | 1900 | 3300 |
| Protease at Product pH [nkat/L] | 46 | 97 |
| Protease at Protease pH [nkat/L] | 2407 | 10037 |

Example 4

In this example IgG recovery from a precipitate was compared by i) dissolving the precipitate in a fixed volume of 220 mM sodium acetate (pH 4.8±0.2) resulting in a final dilution factor of 6 and recovering dissolved protein using depth filtration; ii) dissolving the precipitate in 220 mM sodium acetate (pH 4.8±0.2) and recovering dissolved protein using the continuous extraction process of the invention to achieve a final dilution factor of 31; and iii) using the continuous extraction process of the invention whereby the suspension in the first tank was continuously replenished with fresh buffer to achieve a second dilution factor of 31.

Part i: 1 kg of the same lot of precipitate was suspended in 5 kg of 220 mM sodium acetate (pH 4.8±0.2), using the same impeller mixer (ID 10 cm) to give a final dilution factor of 6 (i.e. 1 kg of the precipitate dissolved in 5 kg of buffer). The suspension was mixed for 8 hours. Prior to depth filtration, filter aid (FA=10 g/kg of Celpure C100, Advanced World Mineral) was added and mixed for 30 min. The depth filtration was performed using combined filter sheets (Polypropylene from Dolder CH, Cellulose, CH9 from Filtrox) in a filter press (20×20 cm frames; from Filtrox) at a maximum pressure of 2.5 bar. The filter area used was 3200 cm$^2$. After the filtration was finished the post wash was started using 2.5 L of the resuspension buffer. This resulted in a total filtrate of 6.9 L and protein concentration of 18 g/L. Protein concentration was determined by Kjeldahl, Biuret and A280 assays. Finally, the filtrate was further concentrated to 20 g/L, using an ultrafiltration membrane having an average molecular weight cut-off value of 10 kD as described above. The yield in a final ultra-filtrate volume of 5.9 L and protein concentration of 20.7 g/L (Table 7).

Part ii: An amount of 1 kg of frozen protein-comprising precipitate in form of a precipitate containing around 100 g filter aid, from Kistler-Nitschman process (KN), was resuspended in 220 mM sodium acetate (pH 4.8±0.2) buffer for 30 min using an impeller mixer (ID 10 mm) to give a first dilution factor of 10 (i.e. 2 kg of the precipitate dissolved in 18 kg of buffer). The suspension in the first tank (20 L working volume) was pumped using a diaphragm pump at a flow rate of 1000 mL/min into the first dynamic filtration process unit. The process unit contained a double layer ceramic-based membrane disc (upper membrane layer 80 nm and lower layer 100 nm). The ceramic filter disc 152 (KERAFOL Keramische Folien GmbH, 92676 Eschenbach) had a diameter of 152 mm; thickness of 4.5 mm; and membrane surface area of 360 cm$^2$. The tangential speed of the disc was approximately 7 m/s at 60 Hz (equivalent to 800 rpm). An average filtration rate was set to approximately 200 ml/min.

Once the first process unit was filled, the suspension was circulated for 10-15 minutes under constant pressure of 1 bar (range: 0 to 2 bar) using the overflow valve (which modulates the return flow of first retentate from the first process unit to the first tank). At this point the continuous extraction process was initiated with the transmembrane pressure (TMP) maintained between 0.5-1.5 bar. The first permeate was collected in a second tank (20 L working volume) at a flow rate 100-200 mL/min. The unfiltered retentate suspension flowed back to the first tank, at a flow rate of 800-900 mL/min, through the regulated outlet valve. When a defined volume (2000-4800 mL) was collected in the second tank (=filtrate tank), the ultrafiltration (second filtration unit) using a 0.2 m$^2$, cut-off 10 kD, Ultracel®/or Biomax® filter (Milipore) was started. The transmembrane pressure (TMP: 0.8-1.5 bar) was set such that the permeate flow rate of the UF system was similar to the permeate filtrate flow rate (100-200 mL/min) to ensure a continuous extraction process. The permeate of the UF-second filtration unit was returned to the first tank at a flow rate of 100-200 mL/min. After 4 hours the filtration was stopped, wherein the predetermined value of protein concentration in the first tank (suspension tank=feed tank) was less than 0.1 g/L. This equates to a final dilution ratio of 1:31. The ultrafiltration process was continued until the protein concentration reached 20 g/L. During this final concentration, the second permeate was sent to waste. The final ultra-filtrate volume was 7.3 L at a protein concentration of 21.4 g/L (Table 7). The protein concentration was determined by the Kjeldahl assay.

Part iii: In a third part of this experiment, the first filtration unit was used as a stand-alone system (i.e. disconnected from second UF system). An amount of 1 kg of the same precipitate was resuspended in 5 kg to give a dilution factor of 6 (i.e. 1 kg of the precipitate dissolved in 5 kg of buffer), wherein the pH of the suspension was about 4.6 to 5.0. All other parameters for this experiment were the same as described in part ii) with the exception that fresh buffer was added to the first tank instead of permeate from the UF system. Once the first filtration unit was filled, the suspension was recirculated for 10-15 minutes under constant pressure of 1 bar (range: 0 to 2 bar) using the overflow return valve before starting the continuous extraction process. The filtrate was collected in a second tank (50 L working volume) at a flow rate 100-200 mL/min. The unfiltered suspension flowed back to the first tank, at a flow rate of 800-900 mL/min, through the regulated return valve. When a defined volume (2000-4800 mL) was collected in the second tank (=filtrate tank) fresh buffer was added to the first suspension tank at a flow rate similar to that of the first permeate filtrate flow rate (i.e. 100-200 mL/min). After about 4 hours the filtration was stopped, wherein the predetermined value of protein concentration in the first tank (suspension tank=feed tank) was less than 0.1 g/L. The volume of collected filtrate was around 31 L at protein concentration of 4.8 g/L. This volume is equal to final dilution ratio of 1:31. The filtrate was further concentrated to a protein concentration of 20.6 g/L to give a final volume of 7.2 L (Table 7).

The results of the IgG yield are shown in Table 7. The IgG yield according to the present invention method (which involves a continuous extraction and filtration process) gave a higher yield than the prior art method. As explained above, by using the extraction and filtration method as disclosed in the present invention, a change in the concentration by increasing the volume (or final dilution factor) is achieved, whereby the dissolution equilibrium is shifted in favour of increased extraction of immunoglobulin G to achieve a higher overall yield.

TABLE 7

Comparison of IgG yield between current and new process at different process steps.

| | Control Part i) | Continuous recovery process Part ii) | Continuous recovery process Part iii) |
|---|---|---|---|
| Initial dilution factor | 1:6 | 1:10 | 1:6 |
| Initial dissolution time (h) | 8 | 0.5 | 0.5 |
| Volume of suspension (L) | 6 | 10 | 6 |
| Protein concentration in suspension (g/L) | 24.3 after 8 h | 10.9 after 0.5 h | 22.1 after 0.5 h |
| Final dilution factor | 1:6 | 1:31 | 1:31 |
| Process time for extraction and filtration (h) | 9 | 4.5 | 4.5 |
| Filtrate volume (L) including post wash for the prior art | 6.9 | Not applicable | 31 |
| Protein conc. (g/L) | 18.0 | Not applicable | 4.8 |
| Total protein (g) | 123.6 | Not applicable | 148.8 |
| Volume post UF (L) | 5.9 | 7.1 | 7.2 |
| Protein conc. post UF (g/L) | 20.7 | 21.4 | 20.6 |
| Protein yield post UF (g/L PEQ) | 12.1 | 14.9 | 14.5 |
| IgG yield post UF (g/L PEQ) | 6.1 | 7.3 | 7.2 |

(Initial dissolution time: is the mixing time prior to the start of the continuous extraction and filtration unit; PEQ stands for plasma equivalent i.e. the amount of IgG from each liter of plasma).

Examples: 5, 6 and 7

In these examples the impact of rotation speed of the rotating filter discs in the first process unit and the overall recirculation volume (final dilution factor) on the protein yield in the second tank was investigated. Table 8 provides an overview of the conditions used.

The results show that the higher the speed of rotation of the discs and the higher the recirculation volume the higher the extracted target proteins recovered in the second tank without increasing co-extraction of the unwanted impurities such as IgA, IgM, lipid and high molecular weight proteins.

Example 5A

For the experiments Cohn I+II+III paste (1 kg containing 120 gram of Celpure C100) was suspended at a first dilution ratio of 1:6 in 10 mM sodium acetate and 10 mM Sodium dihydrogen phosphate dihydrate, pH 4.3-4.4 buffer at 4° C. in the first tank. The suspension in the first tank was stirred at 4° C. with a paddle stirrer for approximately 15-20 hours. Prior to starting the experiments the first filtration unit (a Novoflow dynamic filtration device containing three ceramic filters with 0.2 µm membranes; filter area=0.1 m$^2$) was stored overnight in cold water (1° C.). At the start of the experiments the water was drained from the unit and the suspension was fed into the unit. The suspension was then recirculated for several minutes between the first tank and the first process unit prior to beginning the filtration process. The remaining suspension was gradually added to the first process unit during the filtration process. The ceramic filters in the first process unit were operated at a rotation speed of 1200 rpm and a TMP of 1.2 bar. The permeate from the first process unit was collected in a second tank and then fed into a second unit referred to as the UF/DF unit. The UF/DF unit was a Novoflow dynamic filtration device containing 6 ceramic disks, with 7.0 nm membranes; filter area 0.2 m$^2$. The permeate flow rate of the UF/DF system was 50-70 mL/min. The UF/DF system was started once the first filtrate was collected in the second tank. The retentate of the UF/DF system flowed back into the second tank while the permeate flowed back into the first tank. The volume of permeate fed back into the first tank contributed to the overall volume liquid mixed with the paste (i.e. the final dilution factor). In this experiment, the overall recirculation volume was 107 L per kg of paste (i.e. 1:107 final dilution factor).

Example 5B

In this Example the same procedure was used as described in Example 5A with the exception that the overall recirculation volume was 16 L/kg paste.

Example 6A

In this Example the same procedure was used as described in Example 5A with the exception that the rotation speed of the ceramic filters in the first process unit were operated at 1000 rpm and the overall recirculation volume was 102 L/kg paste.

Example 6B

In this Example the same procedure was used as described in Example 6A with the exception that the overall recirculation volume was 16 L/kg paste.

Example 7A

In this Example the same procedure was used as described in Example 6A with the exception that the the rotation speed of the ceramic filters in the first process unit were operated at 800 rpm and the overall recirculation volume was 93 L/kg paste.

Example 7B

In this Example the same procedure was used as described in Example 7A with the exception that the overall recirculation volume was 16 L/kg paste.

Table 8 provides the experimental parameters and the target protein yield in the second tank following the filtration process.

Impurities were determined by nephelometry, ELISA (IgA, IgM), or enzyme test methods (lipids). The results showed that no significant increases in impurities were observed, but as is clearly shown in Table 8, the protein yield as well as the IgG yield significantly increased with higher rotation speeds, and the yields of both protein and IgG were significantly higher when using a high final dilution factor (Examples 5A, 6A, 7A), as compared to a low final dilution factor (Examples 5B, 6B, 7B)

Example 8A and 8B

In this example the dynamic cross flow filtration process was compared in the presence (Example 8A) and absence (Example 8B) of filter aid. The filter aid used was (Celpure C300; Advanced Minerals).

For the experiments Cohn I+II+III paste (1.2 kg for Example 8A and 1.5 kg for Example 8B was used). Each kilogram of paste contains 120 grams of filter aid. The paste was resuspended at an initial ratio of 1:6 in 10 mM sodium acetate & 10 mM sodium dihydrogen phosphate dihydrate, pH 4.3-4.4 buffer at 4° C. The suspensions were stirred at 4° C. with a paddle stirrer for approximately 15-20 hours. Prior to starting the experiments the first filtration unit (a Novoflow dynamic filtration device containing three ceramic filter 0.2 μm membranes; filter area=0.1 m$^2$) was stored overnight in cold water (1° C.). At the start of the experiments the water was drained and the suspension was fed into the dynamic filter device. The suspension was then recirculated for several minutes between the first tank and the device prior to beginning the filtration process. The remaining suspension was gradually added during the filtration processes (the ceramic filters were operated at 1200 rpm with a TMP of 1.2 to 1.6 bar. In each experiment, about 600 ml of buffer was exchanged 16-18 times. This corresponds to a buffer amount of about 9.6-10.8 L and serves to simulate the buffer recovery of the ultrafiltration/diafiltration unit during online operation. The filtrates were collected in an ice-cooled container under stirring (paddle stirrer) and after the filtrations were completed the filtrates were stirred for a further hour. Subsequently, the filtrates were concentrated to 20 g/L (±5 g/L) using an Äkta Crossflow device.

| Example | 5A | 5B | 6A | 6B | 7A | 7B |
|---|---|---|---|---|---|---|
| Rotation speed (rpm) | 1200 | 1200 | 1000 | 1000 | 800 | 800 |
| Amount of Paste (kg) | 1 | 1 | 1 | 1 | 1 | 1 |
| First dilution factor (Paste:buffer) | 1:6 | 1:6 | 1:6 | 1:6 | 1:6 | 1:6 |
| Final dilution factor = Overall Recirculation volume (L/kg paste | 107 | 16 | 102 | 16 | 93 | 16 |
| Membrane area (m$^2$) | 0.1 | 0.1 | 0.1 | 0.1 | 0.1 | 0.1 |
| Filtration membrane | Ceramic | Ceramic | Ceramic | Ceramic | Ceramic | Ceramic |
| Pore diameter (μm) | 0.2 | 0.2 | 0.2 | 0.2 | 0.2 | 0.2 |
| Transmembrane Pressure TMP (bar) | 1.2 | 1.2 | 1.2 | 1.2 | 1.2 | 1.2 |
| UF/DF | | | | | | |
| Membrane area (m$^2$) | 0.2 | 0.2 | 0.2 | 0.2 | 0.2 | 0.2 |
| Pore diameter (nm) | 7 | 7 | 7 | 7 | 7 | 7 |
| Membrane type | MgAl$_2$O$_4$ | MgAl$_2$O$_4$ | MgAl$_2$O$_4$ | MgAl$_2$O$_4$ | MgAl$_2$O$_4$ | MgAl$_2$O$_4$ |
| Transmembrane Pressure TMP (bar) | 1.6 | 1.6 | 1.6 | 1.6 | 1.6 | 1.6 |
| Protein Yield (%)* | 96.2 | 92.2 | 95.5 | 91.3 | 92.0 | 87.8 |
| IgG Yield (%)* | 98.9 | 95.6 | 97.4 | 95.2 | 95.1 | 94.4 |

MgAl$_2$O$_4$ = Magnesium Aluminium Oxide
*The protein yield is calculated in relation to the starting suspension before the start of the continuous filtration process. The protein-and IgG yield in suspension was set as 100%, (100% total protein in suspension = 13.29 g protein/L plasma equivalent) and (100% total IgG in suspension = 7.34 g IgG/L plasma equivalent)

In Example 8B the filter aid was removed using a Mecaplex pressure filtration sleeve and polypropylene filter layers located between the first tank and the first filtration unit. All other conditions were the same as described in Example 8A.

Figure 2:
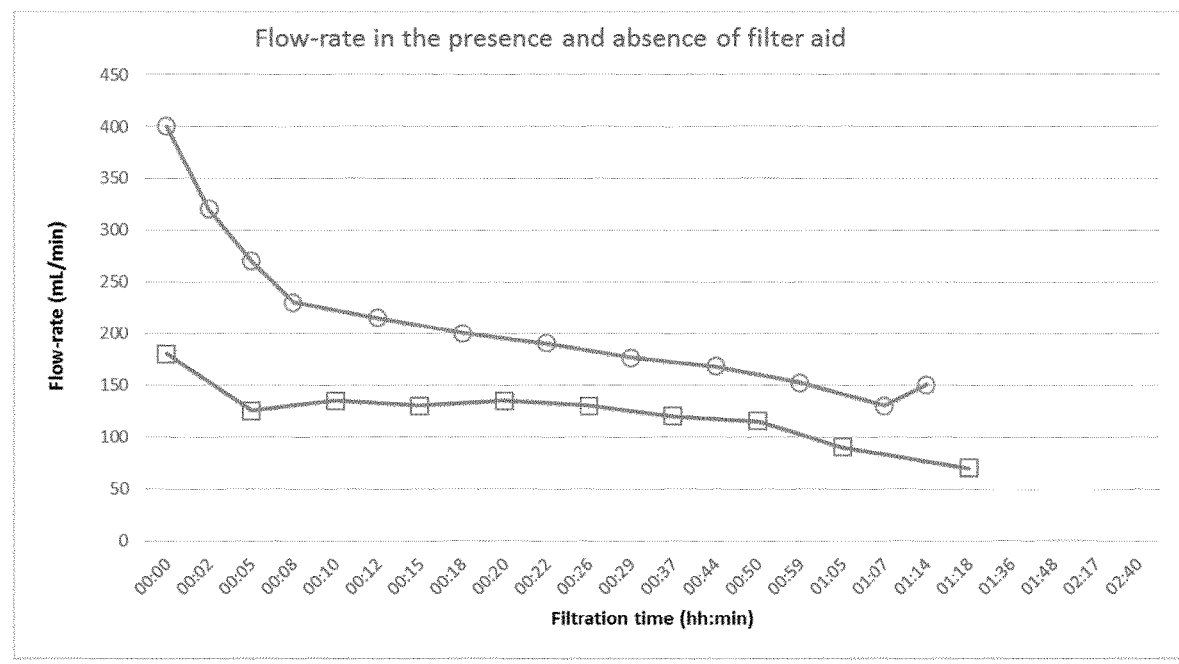
FIG. 2 shows the flow rate over time through the first filtration unit in the presence (squares) and absence (circles) of filter aid.

The experiments demonstrated that the removal of the filter aid resulted in a higher filtration rate through the first filtration unit (FIG. 2). In addition the total protein and IgG recoveries in the filtrates were similar irrespective of the presence or absence of the filter aid. Moreover the removal of the filter aid prior to the first filtration unit also assisted with the removal lipids and other hydrophobic molecules present in the suspensions from the filtrate (data not shown). Thus the filtrate obtained from the first filtration unit when operated in the absence of the filter aid remained more stable (i.e. the filtrate turbidity was relatively lower and remained stable upon storage as compared to the filtrate obtained with the first filtration unit operated in the presence of filter aid). These results further suggest that removal of the filter aid prior to the first filtration unit will improve the throughput capability of the system.

The invention claimed is:

1. A method for extracting a protein of interest from a precipitate, comprising:
   a. mixing the precipitate with a liquid in a first tank to form a suspension having a first dilution factor;
   b. feeding the suspension into a first filtration unit comprising a dynamic filter element adapted to produce a first retentate and a first permeate enriched with the protein of interest;
   c. diluting the suspension in the first tank by adding liquid to a second dilution factor, optionally by streaming the first retentate into the first tank; and
   d. recovering the first permeate enriched with the protein of interest in a second tank,
   wherein steps b and c are repeated until one or both of (i) a final dilution factor has been achieved in the first tank and (ii) a protein concentration of the suspension in the first tank of 0.001 g/L to 0.1 g/L has been achieved.

2. The method according to claim 1, wherein the first dilution factor is from 1 to 10.

3. The method according to claim 1, wherein steps b and c are repeated until a final dilution factor of is from 6 to 70 has been achieved in the first tank.

4. The method according to claim 1, wherein steps b and c are repeated until a protein concentration of the suspension in the first tank of 0.001 g/L to 0.1 g/L has been achieved.

5. The method according claim 1, wherein the precipitate is an intermediate product of an alcohol fractionation process of blood plasma.

6. The method according to claim 5, wherein the intermediate product is selected from the group consisting of Cohn Fraction I (Fr I), Cohn Fraction II+III (Fr II+III), Cohn Fraction I+II+III (Fr I+II+III), Kistler/Nitschmann Precipitate A (KN A), and combinations of KN A and one or more of Fr I, Fr II+III and Fr I+II+III.

7. The method according to claim 1, wherein the precipitate is a culture supernatant or a fermentation product.

8. The method according to claim 1, wherein the protein of interest is an immunoglobulin (Ig).

9. The method according to claim 1, wherein the first filtration unit comprises a pressure vessel.

10. The method according to claim 9, wherein the first filtration unit is equipped with rotating filter discs comprising ceramic membranes and optionally baffles for turbulence mixing of the content of the first filtration unit.

11. The method according to claim 10, wherein a transmembrane pressure across the ceramic membrane is from 0.1 bar to 2.5 bar.

12. The method according to claim 1, wherein the dynamic filter element is a dynamic cross flow filter element.

13. The method according to claim 12, wherein the dynamic cross flow filter element is a rotational cross-filter element having a rotating speed of is from about 600 rpm to about 1200 rpm.

14. The method according to claim 1, wherein the temperature in the first filtration unit is controlled at 2° C. to 25° C.

15. The method according to claim 1, wherein the precipitate comprises a filter aid.

16. The method according to claim 15, wherein the filter aid is removed prior to the first filtration.

17. The method according to claim 1, wherein the extraction process is further assisted by regulating one or more of a flow rate of the suspension in the first filtration unit, a residence time of the suspension in the first filtration unit, a flow rate of the first retentate, and a flow rate of the first permeate.

18. The method according to claim 1, wherein the suspension has a pH of from about 3.0 to 9.0.

19. The method according to claim 1, wherein the precipitate has a total protein concentration of about 0.5 to 6.5% w/v.

20. The method according to claim 1, wherein the liquid comprises a buffer comprising one or more of sodium acetate, sodium phosphate, and citric acid.

21. The method according to claim 1, wherein the precipitate is added to the first tank in the form of a suspension, pellet or paste.

22. The method according to claim 1, wherein the product of the method is subjected to further processing including one or more of chromatography steps, virus inactivation steps, concentration and formulation such that the end product is suitable for administration to a subject.

23. A method for extracting a protein of interest from a precipitate, comprising:
   a. mixing the precipitate with a liquid in a first tank to form a suspension having a first dilution factor;
   b. feeding the suspension into a first filtration unit comprising a dynamic filter element adapted to produce a first retentate and a first permeate enriched with the protein of interest;
   c. diluting the suspension in the first tank by adding liquid to a second dilution factor, optionally by streaming the first retentate into the first tank;
   d. recovering the first permeate enriched with the protein of interest in a second tank;
   e. subjecting the first permeate in the second tank to a continuous concentration process in a second filtration unit comprising a cross flow filter element, thereby producing a second retentate enriched with the protein of interest and a second permeate depleted of the protein of interest;
   f. optionally diluting the suspension in the first tank by streaming the second permeate to the first tank, thereby diluting the suspension to a further dilution factor; and
   g. one or both of (i) returning second retentate enriched with the protein of interest to the second tank and (ii) collecting second retentate enriched with the protein of interest;
   wherein either steps b and c or steps b-f are repeated until one or both of (i) a final dilution factor has been achieved in the first tank and (ii) a protein concentration of the suspension in the first tank of 0.001 g/L to 0.1 g/L has been achieved.

24. The method according to claim 23, wherein the first permeate is continuously fed into the concentration process of step e.

25. The method according to claim 23, wherein the concentration process of step e is an ultrafiltration performed in the second filtration unit.

26. The method according to claim 23, wherein the first permeate is collected in the second tank at step d, and once the suspension of the first tank is completely filtrated, the first permeate from the second tank is subjected to the continuous concentration process of step e.

27. The method according to claim 23, wherein the dynamic filter element or the cross-flow filter element comprises a filtration membrane having an average pore size of 5 nm to 5000 nm.

28. The method according to claim 23, wherein a flow velocity of the first permeate and the second permeate are controlled such that a constant product volume is maintained in the second tank.

29. An industrial scaled method for extracting a protein of interest in high yield from a precipitate, comprising:
 a. mixing the precipitate with a liquid in a first tank to form a suspension having a first dilution factor;
 b. continuously feeding the suspension into a first filtration unit comprising a rotational cross flow filter element comprising a filter disc having a ceramic membrane with an average pore size between 5 nm and 5000 nm, the filter element adapted to produce a first retentate, and a first permeate enriched with the protein of interest;
 c. diluting the suspension in the first tank by adding liquid to a second dilution factor in part by streaming the first retentate into the first tank;
 d. recovering the first permeate enriched with the protein of interest in a second tank;
 e. subjecting the first permeate in the second tank to a continuous concentration process in a second filtration unit comprising a cross flow filter element, thereby producing a second retentate enriched with the protein of interest and a second permeate depleted of the protein of interest;
 f. optionally diluting the suspension in the first tank by continuously streaming the second permeate to the first tank, thereby diluting the suspension to a further dilution factor; and
 g. one or both of (i) returning second retentate enriched with the protein of interest to the second tank and (ii) collecting second retentate enriched with the protein of interest,
wherein either steps b and c or steps b-f are repeated until one or both of (i) a final dilution factor has been achieved in the first tank and (ii) a protein concentration of the suspension in the first tank of 0.001 g/L to 0.1 g/L has been achieved.

* * * * *